(12) United States Patent
Takashima et al.

(10) Patent No.: US 6,653,285 B1
(45) Date of Patent: Nov. 25, 2003

(54) MODULATORS OF POLYSACCHARIDES AND USES THEREOF

(75) Inventors: Akira Takashima, Coppel, TX (US); Mark E. Mummert, Dallas, TX (US); Mansour Mohamadzadeh, Plano, TX (US)

(73) Assignee: The University of Texas System, Austin, TX (US)

( * ) Notice: Subject to any disclaimer, the term of this patent is extended or adjusted under 35 U.S.C. 154(b) by 0 days.

(21) Appl. No.: 09/532,709

(22) Filed: Mar. 22, 2000

Related U.S. Application Data
(60) Provisional application No. 60/126,475, filed on Mar. 26, 1999.

(51) Int. Cl.[7] .................. A61K 38/00; C07K 16/00
(52) U.S. Cl. ..................... 514/14; 514/23; 530/327; 530/300
(58) Field of Search .................. 514/14, 23; 530/327, 530/300

(56) References Cited

U.S. PATENT DOCUMENTS
5,981,478 A * 11/1999 Ruoslahti .................. 514/10

FOREIGN PATENT DOCUMENTS
| EP | 0950708 A2 | 10/1999 |
| WO | WO 93/21312 A1 | 10/1993 |
| WO | WO 02/28415 A1 * | 4/2002 |

OTHER PUBLICATIONS
Van Kuppelt et al., (1998), *J. Biol. Chem.*, 273(21):12960–12966.
Liang et al., (1997),*FEBS.*, 407:169–172.
Kubens et al., (1997), *Cancer Lett.*, 118:189–200.
Henri Becquerel, Role of hyaluronic acid in the arterial response to angioplasty, 1998, J. Path. Biol. 46: 561–570.*
Dougherty et al. (Mar. 25, 1994), "Ligand Binding Specificity of Alternatively Spliced CD44 Isoforms–Recognition and Binding of Hyaluronan by CD44R1." *The Journal of Biological Chemistry*, vol. 269(12):9074–9078.
Levesque et al. (1996), "In Vitro Culture of Human Peripheral Blood Monocytes Induces Hyaluronan Binding and Up–Regulates Monocyte Variant CD44 Isoform Expression." *The Journal of Immunology*, vol. 156:1557–1565.
Steinman, Ralph (1991), "The Dendritic Cell System and its Role in Immunogenicity." *Ann. Rev. Immunol.*, vol. 9:271–296.
Turley et al. (Mar. 1991), "Hyaluronan and a Cell–associated Hyaluronan Binding Protein Regulate the Locomotion of Ras–transformed Cells." *The Journal of Cell Biology*, vol. 112(5):1041–1047.
Barbas et sl. (1992) "Semisynthetic combinatorial antibody libraries: A chemical solution to the diversity problem." *Proc. Natl. Acad. Sci. USA*, vol. 89:4457–4461.
Garrard et al. (1993) "Selection of an anti–IGF–1 Fab from a Fab phage library created by mutagenesis of multiple CDR loops." *Gene*, vol. 128:103–109.

* cited by examiner

*Primary Examiner*—T. D. Wessendorf
(74) *Attorney, Agent, or Firm*—Carol L. Francis; Bozicevic, Field & Francis LLP

(57) ABSTRACT

The present invention provides peptides with a specific affinity for glycosaminoglycan molecules. These peptides may have any number of functions, including but not limited to use as inhibitors of glycosaminoglycan-mediated processes, enhancers of glycosaminoglycan-mediated processes, and as molecular probes to identify the presence of a specific glycosaminoglycan. Peptides of the invention may be directed against any glycosaminoglycan, including hyaluronic acid, chondroitin sulfate A, chondroitin sulfate C, dermatan sulfate, heparin, keratan sulfate, keratosulfate, chitin, chitosan 1, and chitosan 2. These isolated peptides may have therapeutic uses in the treatment or prevention of diseases involving infection, inflammatory diseases, cancer, infections, etc. The peptides may also have other biological functions such as contraception.

23 Claims, 10 Drawing Sheets

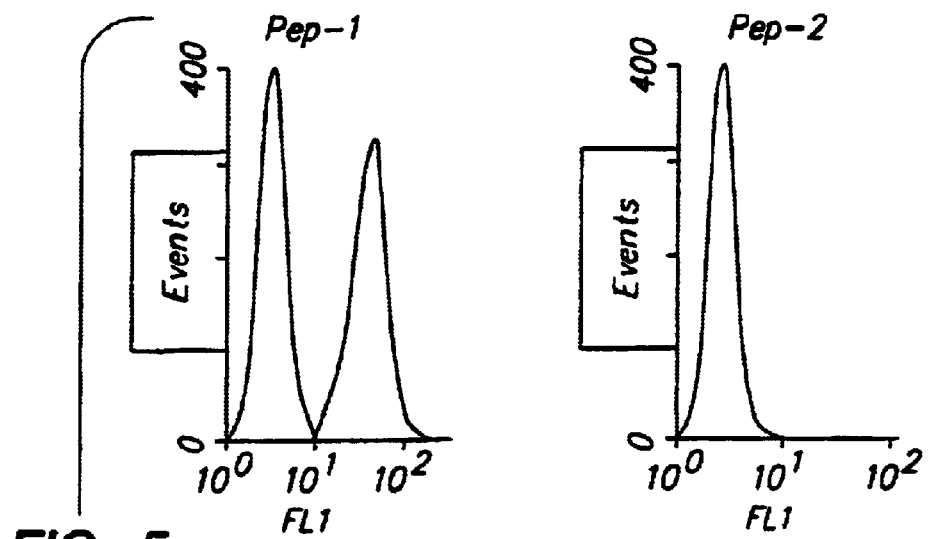
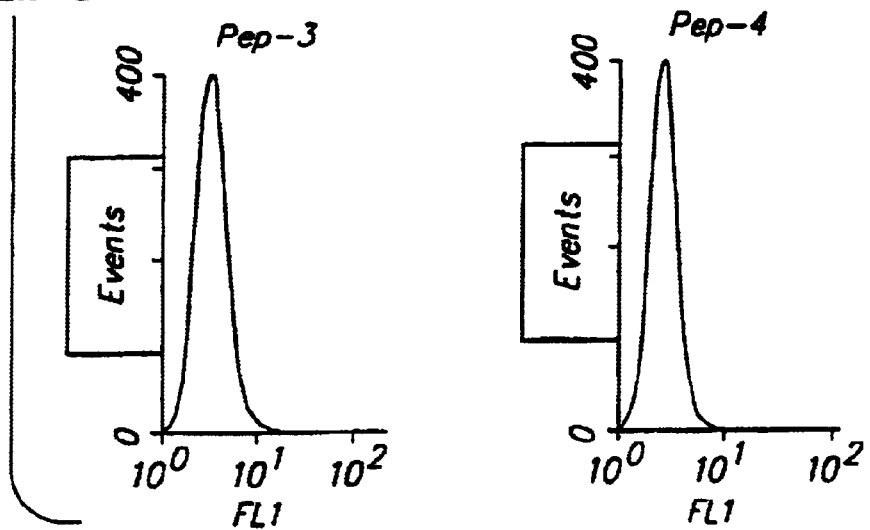
FIG. 5
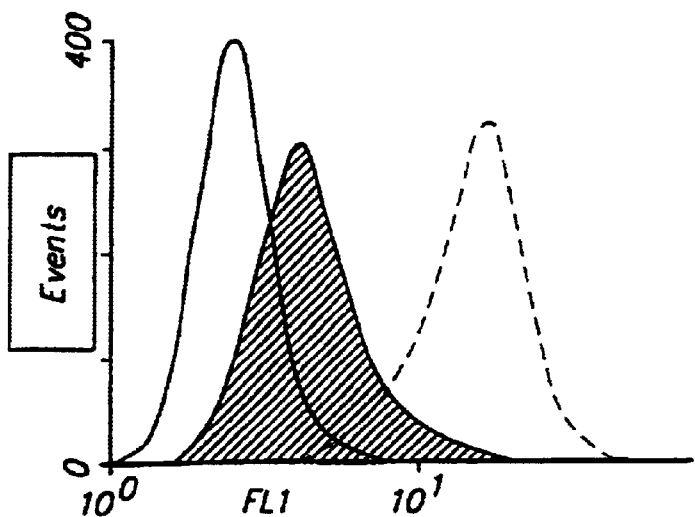
FIG. 6

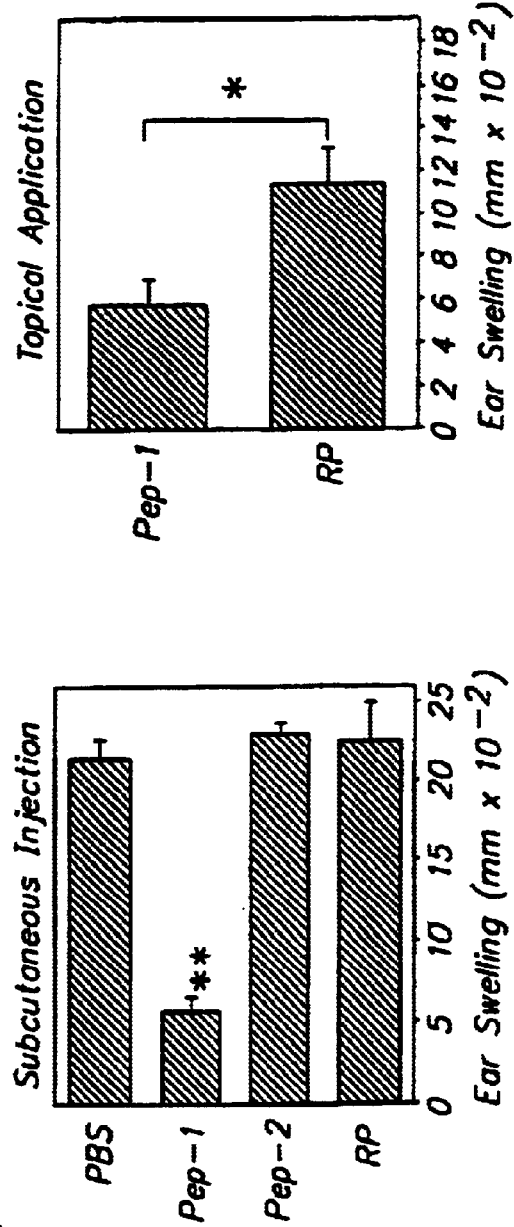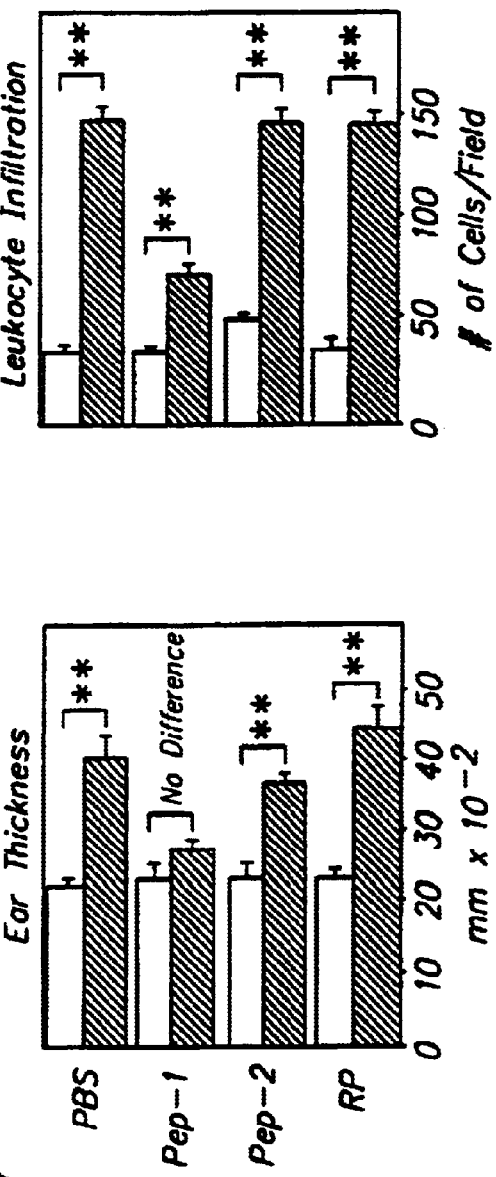

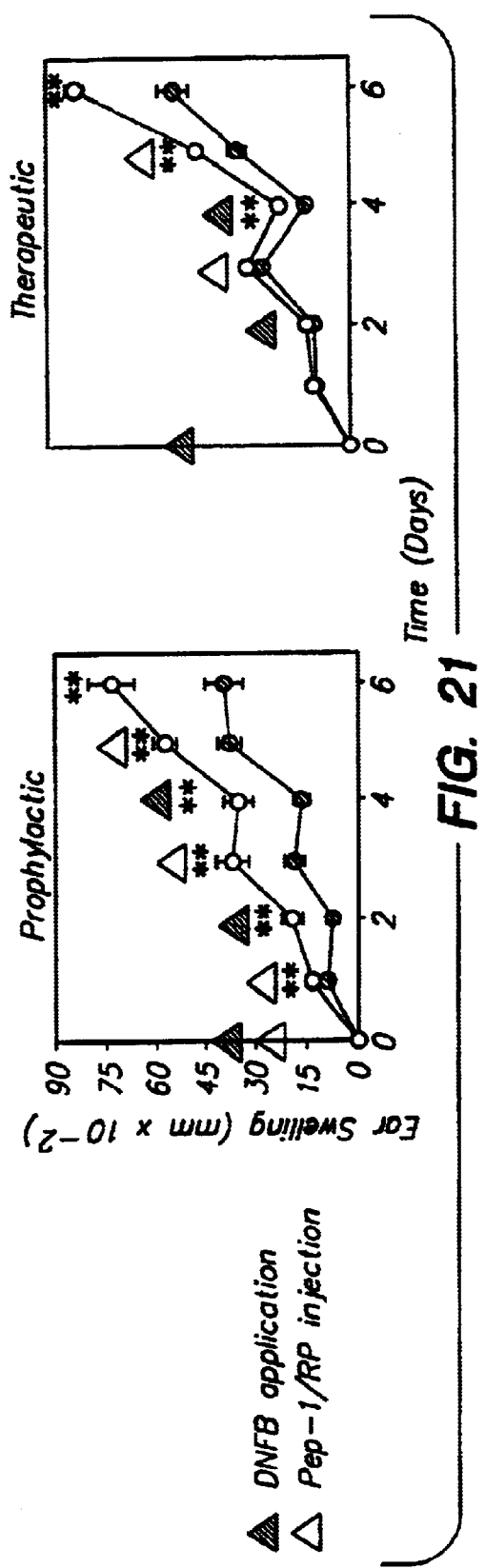
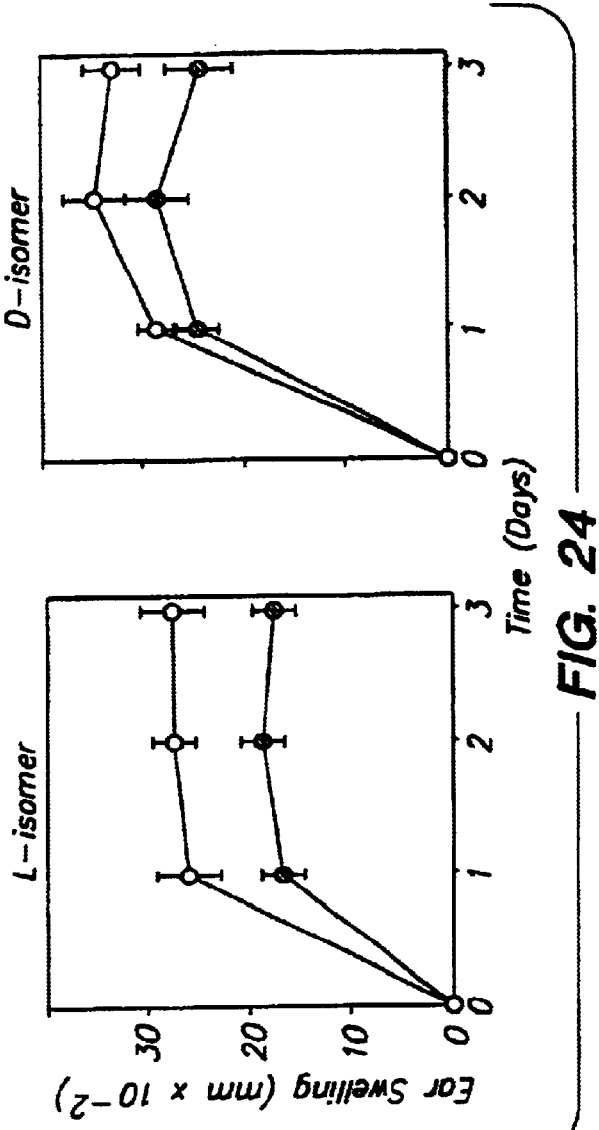
FIG. 21
FIG. 24

```
SEQUENCE LISTING

<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Gly Ala His Trp Gln Phe Asn Ala Leu Thr Val Arg
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: synthetic peptide

<400> SEQUENCE: 2

Thr Ser Tyr Gly Arg Pro Ala Leu Leu Pro Ala Ala
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: synthetic peptide

<400> SEQUENCE: 3

Met Asp His Leu Ala Thr Phe Arg Pro Ala Ile
```

```
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: synthetic peptide

<400> SEQUENCE: 4

```
Thr Leu Arg Ala Ile Trp Pro Met Trp Met Ser Ser
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: synthetic peptide

<400> SEQUENCE: 5

```
Ile Pro Leu Thr Ala Asn Tyr Gln Gly Asp Phe Thr
1               5                   10
```

<210> SEQ ID NO 6
<211> LENGTH: 16
<212> TYPE: PRT
<213> ORGANISM: Artificial Sequence
<220> FEATURE:
<223> OTHER INFORMATION: synthetic peptide

<400> SEQUENCE: 6

```
Ser Ala Thr Pro Ala Ser Ala Pro Tyr Pro Leu Ala Gly Gly Gly Ser
1               5                   10                  15
```

<210> SEQ ID NO 7
<211> LENGTH: 12
<212> TYPE: PRT
<213> ORGANISM: Artificial Sequence
<220> FEATURE:
<223> OTHER INFORMATION: synthetic peptide

<400> SEQUENCE: 7

```
Gly Ala Ala Trp Gln Phe Asn Ala Leu Thr Val Arg
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

```
Gly Ala His Trp Gln Phe Ala Ala Leu Thr Val Arg
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: synthetic peptide

<400> SEQUENCE: 9

```
Gly Ala His Trp Gln Phe Asn Ala Leu Thr Val Ala
1               5                   10
```

```
<210> SEQ ID NO 10
<211> LENGTH: 4
<212> TYPE: PRT
<213> ORGANISM: Artificial Sequence
<220> FEATURE:
<223> OTHER INFORMATION: Spacer sequence

<400> SEQUENCE: 10

Gly Gly Gly Ser
 1
```

MODULATORS OF POLYSACCHARIDES AND USES THEREOF

CROSS-REFERENCE TO RELATED APPLICATION

This application claims the benefit of U.S. provisional application serial No. 60/126,475, filed Mar. 26, 1999, which application is hereby incorporated by reference.

GOVERNMENT RIGHTS

The United States Government may have certain rights in this application pursuant to Immunodermatology Training Grant No. AR07341.

FIELD OF THE INVENTION

The invention relates to peptide inhibitors of glycosaminoglycans. This invention also relates to formulations, uses and methods of identifying such inhibitors.

BACKGROUND OF THE INVENTION

The extracellular matrix (ECM) is a dynamic assemblage of interacting molecules that regulate cell functions and interactions in response to stimulation. One class of extracellular matrix macromolecules, the glycosaminoglycans, are molecules known to be involved in a wide array of both normal and abnormal biological processes, including cell migration, differentiation, proliferation, immune response and cytoskeletal organization.

The glycosaminoglycan hyaluronan (HA) is a repeating disaccharide of $[GlcNAc\beta1-4GlcUA\beta1-3]_n$ that exists in vivo as a high molecular weight linear polysaccharide. HA is found in mammals predominantly in connective tissues, skin, cartilage, and in synovial fluid, and is also the main constituent of the vitreous of the eye. In connective tissue, the water of hydration associated with HA creates spaces between tissues, thus creating an environment conducive to cell movement and proliferation. HA plays a key role in biological phenomena associated with cell motility including rapid development, regeneration, repair, embryogenesis, embryological development, wound healing, angiogenesis, and tumorigenesis (Toole, *Cell Biol. Extracell. Matrix,* Hay (ed), Plenum Press, New York, 1384–1386 (1991); Bertrand et al. *Int. J. Cancer* 52:1–6 (1992); Knudson et al, *FASEB J.* 7:1233–1241 (1993)). HA levels have been shown to correlate with tumor aggressiveness (Ozello et al., *Cancer Res.* 20:600–604 (1960); Takeuchi et al., *Cancer Res.* 36:2133–2139 (1976); Kimata et al., *Cancer Res.* 43:1347–1354 (1983)), and can be indicative of the invasive properties of tumor cells. M. M. Knupfer et al., *Anticancer Res* 18:353–6 (1998).

HA is also involved in immune response, and thus may mediate this response in both normal and abnormal biological reactions. Increased binding of HA to one of its receptors, CD44, has been shown to mediate the primary adhesion ("rolling") of lymphocytes to vascular endothelial cells under conditions of physiologic shear stress, and this interaction mediates activated T cell extravasation into an inflamed site in vivo in mice. H. C. DeGrendele, et al., *J. Exp. Med.* 183:1119–1130 (1996); H. D. DeGrendele,et al., *Science* 278:672–675 (1997). H. C. DeGrendele et al., *J. Immunol.* 159:2549–2553 (1997). Alterations in levels of HA and other glycosaminoglycans have also been associated with unwanted immune responses, and may be involved in diseases and disorders such as rheumatoid arthritis, atopic dermatitis, psoriasis, multiple sclerosis, transplantation rejection. For example, HA and other glycosaminoglycans display are altered in autoimiune disorders such as arthritis, and decreased levels of both hyaluronic acid and chondroitin 6-sulfate have been found in the diseased synovial fluid of both adults with rheumatoid arthritis (A. Bensouyad et al., *Ann Rheum Dis* 49:301–7 (1990)) and children with juvenile rheumatoid arthritis (P. F. Spelling et al. *Clin Exp Rheumatol* 9:195–9 (1991)).

Dendritic cells (DC) play essential roles in the induction of cellular immune responses to a variety of relevant antigens. DC are known to play critical roles in the induction of cellular immune responses against a wide variety of antigens of relevance, including chemical haptens, foreign proteins, infectious microbes, and tumor-associated antigens (Steinman, "The dendritic cell system and its role in immunogenicity." *Ann. Rev. Immunol.* 9:271 (1991); Stingl et al., "The Epidermis: An Immunologic Microenvironment In Dermatology in General Medicine." T. B. Fitzpatrick, ed. McGraw Hill and Co., New York, p. 172 (1993)). Interaction between HA, expressed on endothelial cells, and CD44, expressed on activated dendritic cells as well as T cells, and granulocytes, is believed to mediate homing of such leukocytes to their target sites.

Glycosaminoglycans, and particularly HA, are also known to mediate other cellular interactions that involve binding and entry into a cell. For example, HA is involved in infection of mammalian cells by the Human Immunodeficiency Virus (HIV), since HIV is known to bind to HA upon infection. Both HA and monoclonal antibodies to its receptor CD44 were found to inhibit HIV infection of monocytes by monocytotropic HIV. M. C. Levesque and B. F. Haynes, *J. Immunol* 156:1557–65 (1996). HA is also involved in mammalian zygote formation by mediating binding of the oocyte and the sperm. Data suggests that HA in the cumulus matrix may act to prime the fertilizing sperm for induction of the acrosome reaction by constituents of the cumulus and/or zona pellucida. HA is thought to mediate this interaction by binding to the PH-20 protein to increase basal levels of intracellular calcium and thereby potentiate the acrosome reaction. K. Sabeur et al., *Zygote* 6:103–11 (1998). HA mediates sperm motility by enhancing phosphorylation of proteins including HA binding protein. S. Ranganathan et al., *Cell Mol Biol Res* 41:467–76 (1995).

The role of glycosaminoglycans, and particularly hyaluronic acid, in such varying physiological processes make them attractive targets for therapeutic agents. Unfortunately, glycosaminoglycans have been found to be nearly non-antigenic, and very few antibodies that recognize glycosaminoglycans have been isolated. Due to this lack of antigenicity, it has been technically difficult to develop inhibitors or probes of glycosaminoglycans. Thus, there is a need in the art for inhibitors of glycosaminoglycan-mediated processes, and in particular for inhibitors of hyaluronic acid-mediated processes. There is also a need for a method of identifying effective glycosaminoglycan inhibitors in a systematic, reproducible manner.

SUMMARY OF THE INVENTION

The present invention provides peptides with a specific affinity for glycosaminoglycan molecules. These peptides exhibit any number of functions, including but not limited to inhibitors of glycosaminoglycan-mediated processes, enhancers of glycosaminoglycan-mediated processes, and as molecular probes to identify the presence of a specific glycosaminoglycan. Peptides of the invention are administered in order to inhibit, alter the interaction of, or otherwise affect the activity or function of any glycosaminoglycan, including hyaluronic acid, chondroitin sulfate A, chondroitin sulfate C, dermatan sulfate, heparin, keratan sulfate, keratosulfate, chitin, chitosan 1, and chitosan 2. These isolated peptides are formulated and administered by injection for the treatment or prevention of diseases involving viral infection, inflammatory diseases, cancer, infections, etc. Moreover, these peptides are formulated and administered for the stimulation of normal biological responses, such as wound healing, angiogenesis, etc. The peptides of the invention cab be labeled directly or indirectly and as such are useful in in vitro, ex vivo or in vivo probes to determine the presence of a particular glycosaminoglycan in a biological sample and/or patient.

In a preferred embodiment, the invention provides isolated and substantially purified peptides which specifically bind to and as such inhibit or otherwise affect the activity of HA. The isolated peptide inhibitors are characterized by aliphatic or polar aliphatic residues at positions 4, 5 and 6 and/or 9, 10 and 11.

An aspect of the invention is a composition comprising a carrier material and an active ingredient. The active ingredient is characterized by all or any of (1) specifically and selectively binding to a glycosaminoglycan which is preferably hyaluronic acid; (2) inhibiting the normal function of or altering the normal interactions of or otherwise affecting the normal activity of a glycosaminoglycan; (3) having an amino acid sequence corresponding to any of SEQ ID NOS:1, 2, 3, 4 or 5; or (4) having sufficient homology with any of SEQ ID NOS:1, 2, 3, 4 or 5 so as to present a structure characterized by (1) or (2) above.

The invention further provides pharmaceutical and cosmetic compositions containing a peptide that specifically modulates a glycosaminoglycan-mediated activity. The peptides in the pharmaceutical composition are used in conjunction with an acceptable pharmaceutical carrier, to prepare medicinal compositions for the treatment of glycosaminoglycan-mediated disorders in animals, and more preferably mammals, including humans. In a preferred embodiment, the glycosaminoglycan modulated is HA. In a more preferred embodiment, the peptide is an HA inhibitor comprising the sequence of SEQ ID NO:1.

The invention further provides the use of the described isolated peptides in cosmetic compositions, e.g. a topical skin cream, with an acceptable cosmetic carrier. Such topical skin creams may contain additives such as emollients, moisturizers, fragrance, and the like. In a preferred embodiment, the glycosaminoglycan modulated is HA, and the peptide used to modulate the activity is characterized by aliphatic or polar aliphatic residues at positions 4, 5 and 6 and/or 9, 10 and 11. In a more preferred embodiment, the peptide is an HA inhibitor comprising the sequence of SEQ ID NO:1.

The present invention also provides a method of blocking cell migration using peptides with specific affinity for glycosaminoglycan molecules. In one embodiment, the invention provides a method for preventing DC migration from the epidermis by blocking HA-CD44 interaction with a peptide inhibitor of HA. In a preferred embodiment, the peptide used to block the HA-CD44 interaction is comprised of SEQ ID NO:1.

The present invention also provides a method of preventing the induction of immune responses by altering the interaction of glycosaminoglycans and cell receptor molecules. Peptides specific for a glycosaminoglycan can inhibit interaction with cell surface molecules of migratory cells, thus inhibiting the migration process. In one embodiment, peptides specific for HA can inhibit the migration of immune cells by inhibiting interaction with CD44. In another embodiment, peptides that are specific for heparin can inhibit the migration of cells where the migration is dependent on the fibroblast growth factor receptor.

The present invention also provides a method of identifying peptides that specifically bind to a carbohydrate, such as a glycosaminoglycan, using a phage display technology. The method of the invention includes a step of selecting peptides that specifically bind to the carbohydrate of interest by collecting only the clones released from the carbohydrate-coated plates after treatment to neutralize the function of the carbohydrate, e.g. by addition of the same or similar carbohydrate in excess, by enzymatic or non-enzymatic digestion of the carbohydrate, by use of a chelator, and the like.

One aspect of the invention is a composition comprising a pharmaceutically acceptable carrier and an active ingredient have an amino acid sequence defined by a motif ZZZXZZZ where Z is either an aliphatic or polar aliphatic amino acid and X is any amino acid.

One feature of the present invention is that the peptides identified using the method of the invention inhibit glycosaminoglycan-protein interactions by binding to the glycosaminoglycan rather than to the protein with which it interacts.

Another feature of the peptides of the present invention is that they afford better inhibition of glycosaminoglycan-mediated activity than larger, less specific glycosaminoglycan inhibitors such as receptor antibodies, e.g. anti-CD44 antibodies.

An advantage of the peptide modulators of the present invention is that they are more specific than chemical inhibitors of glycosaminoglycans, e.g. tunimycin and H7.

Another advantage of the peptide modulators of the invention is that they are significantly smaller than other inhibitors of glycosaminoglycan-mediated activity, e.g. antibodies or soluble glycosaminoglycan. The smaller size of the peptide allows for better oral and topical formulations.

Another advantage of the present invention is that the peptide inhibitors of the invention is that they are more cost effective to produce than presently available modulators of glycosaminoglycan-protein interactions, e.g. CD44 inhibitors such as anti-CD44 antibodies.

These and other objects, advantages and features of the present invention will become apparent to those persons skilled in the art upon reading the details of the presently described invention.

BRIEF DESCRIPTION OF THE DRAWINGS

FIG. 5 is a set of histograms illustrating binding of Peptides 1–4 to native HA molecule on endothelial cells. Closed histograms represent binding at 62 μM to SVEC 10–40 endothelial cells. Open histograms represent cells incubated with biotinylated RP.

FIG. 6 is a histogram illustrating binding of Peptide 1 to HAase-treated (closed histogram) and mock-treated endothelial cells.

FIG. 19 is a set of bar graphs illustrating the ability of Peptide 1 to decrease ear swelling following administration of DNFB.

FIG. 20 is a set of bar graphs illustrating ear thickness and leukocyte infiltration following administration of DNFB and Peptide 1.

FIG. 21 is a set of line graphs illustrating the prophylactic and therapeutic effects of Peptide 1 and RP with DNFB administration.

FIG. 24 is a set of lines graphs illustrating the ability of both the L-isomer and the D-isomer of Peptide 1 to decrease ear swelling in response to DNFB application.

DESCRIPTION OF THE SPECIFIC EMBODIMENTS

Figure 2:
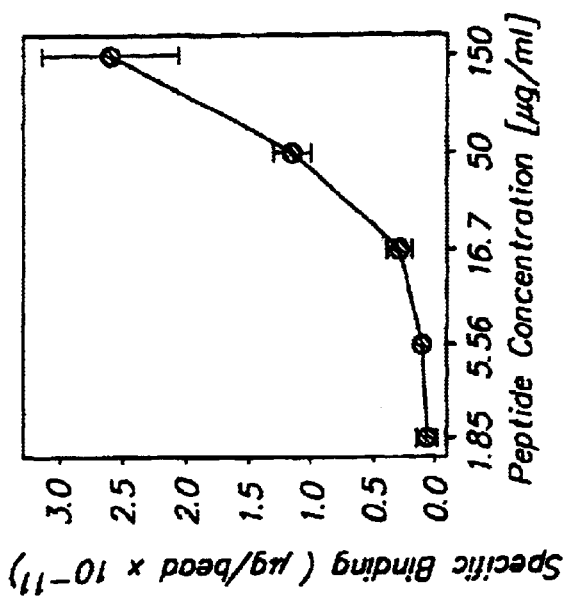
FIG. 2 is a line graph illustrating the titration of Peptide 1 with HA coated beads.

It is to be understood that this invention is not limited to the particular methodology, protocols, peptides, polysaccharides, constructs, and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a construct" includes a plurality of such constructs and reference to "the peptide inhibitor" includes reference to one or more peptide inhibitors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the glycosaminoglycans, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. In one embodiment, "treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease. The invention is directed toward treating patients for biological processes involving cell migration such as inflammation and is particularly directed toward treating cancer cell metastasis. In another embodiment, the term "treatment" as used herein covers any use for inhibiting or enhancing a normal biological process, such as oocyte fertilization.

The term "amino acid" as used herein include the twenty naturally occurring amino acids, including both the L-isomeric and D-isomeric forms. The term also includes alternate amino acid residues, such as hydroxyproline, α-aminoisobutyric acid, sarcosine, citrulline, cysteic acid, t-butylglycine, t-butylalanine, phenylglycine, cyclohexylalanine, β-alanine, 4-aminobutyric acid, and so forth can also be included in the peptide sequence in a completely analogous way. The D forms of the encoded amino acids and of alternate amino acids can, of course, also be employed. The manner of determining relative rate constants, of conducting syntheses, and of conducting selection and analysis is entirely analogous to that described below for the naturally occurring amino acids. Accordingly, the results in terms of the number of rate constants required, the number of representative peptides in the mixture, etc., are also directly applicable to peptides which include as one, or more, or all residues, these nonencoded amino acids.

The term "isolated" means the protein is removed from its natural surroundings. However, some of the components found with it may continue to be with an "isolated" protein. Thus, an "isolated protein" is not as it appears in nature but may be substantially less than 100% pure protein.

The term "phage-display library" as used herein refers to a protein expression library, constructed in either a viral or non-viral expresses a collection of cloned protein sequences such as fusions with a phage coat protein.

The term "glycosaminoglycan" as used herein refers to a macromolecule comprised of carbohydrate. The glycosaminoglycans for use in the present invention may vary in size and be either sulfated or non-sulfated. The glycosaminoglycans which may be targeted using the inhibitors and methods of the invention include, but are not limited to, hyaluronic acid, the chondroitin sulfates, keratan sulfate, chitin and heparin.

By "binds specifically" is meant high avidity and/or high affinity binding of a peptide to a specific epitope, i.e., the epitope of a glycosaminoglycan. Peptide binding to an epitope on this specific polysaccharide is preferably stronger than binding of the same peptide to any other epitope, particularly those which may be present in molecules in association with, or in the same sample, as the specific polysaccharide of interest, e.g., binds more strongly to HA than to other cellular moieties. Peptides that bind specifically to a glycosaminoglycan of interest may be capable of binding other glycosaminoglycan at a weak, yet detectable, level (e.g., 10% or less of the binding shown to the polypeptide of interest). Such weak binding, or background binding, is readily discernible from the specific peptide binding to the glycosaminoglycan of interest, e.g. by use of appropriate controls. In general, peptides of the invention bind to native HA with a binding affinity of $10^7$ liters/mole or more, preferably $10^8$ l/mole or more, even more preferably $10^9$ l/mole or more, are said to bind specifically to HA. In general, a peptide with a binding affinity of $10^4$ l/mole or less is not useful in that it will not bind an epitopes at a detectable level using conventional methodology currently used.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 10 amino acids, preferably at least 12 amino acids, more preferably at least 15 amino acids, and most preferably 35 amino acids.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "neutralized" as used herein refers to treatment of a glycosaminoglycan with an agent such that it no longer is available for interaction with a binding partner, e.g. treatment of a glycosaminoglycan with a digestive enzyme. For example, HA may be neutralized by treatment with an effective amount of hyaluronidase HAase.

Overview of the Invention

Since glycosaminoglycans are nearly non-antigenic, it has been technically difficult to develop inhibitors or probes of glycosaminoglycans. The present invention utilized a modified phage display method to identify small peptides that bind selectively to glycosaminoglycans, e.g. for use as a molecular probes, and to identify peptides that block the function of glycosaminoglycans, e.g. for use as inhibitors. Specifically, the phage display strategy of the present invention has been used to identify peptides that bind selectively to and inhibit the activity of HA.

Many peptides selected by conventional phage display protocols are known to bind non-selectively to polystyrene surfaces. See Adey et al., Gene 156:27 (1995). The method of the present invention circumvents this non-specific binding by selecting peptides that specifically bind to the glycosaminoglycan of interest. The present method involves collection of only the clones released from the glycosaminoglycan-coated plates following treatment to neutralize the carbohydrate, allowing identification of peptides that bind to the glycosaminoglycan substrate, but not to the polystyrene surfaces. Unbound carbohydrate moieties can be neutralized by any treatment known to one skilled in the art to interfere with carbohydrate binding and/or activity, including treatment of the plates with an excess of the same or a similar carbohydrate, treatment with a chelator that prevents binding to the carbohydrate, or preferably treatment with an enzymatic or non-enzymatic compound that digests the unbound carbohydrate. The peptides that have been isolated using the method of the present invention directed against HA were all specific, and none contained the moieties that are commonly found in the polystyrene-binding peptide.

Phage Display Protocol

Peptides with the ability to bind to glycosaminoglycans can be identified and isolated using a phage display peptide library. Libraries for use in the method of the invention are comprised of peptide sequences expressed as fusions with a coat protein of a bacteriophage. The fused protein is displayed on the protein coat of the virion, while the DNA encoding the fusion lies in the virion. Random peptide libraries can be used to screen for peptides that bind to an epitope of interest by exposing the virion library to an immobilized "target" glycosaminoglycan and isolating phage that specifically bind to this glycosaminoglycan.

Scott and Smith (1990) presented a method of defining peptide ligands by using randomly synthesized peptide inserts in bacteriophage. Related methods were published by Cwirla et al. (1990) and by Devlin et al. (1990). Since that time a literature has arisen in which both the original hexapeptide inserts and larger inserts have been used in identifying epitopes recognized by binding entities.

The average size of the peptides in the phage display libraries may vary, but preferably the peptides are at least octapeptides (8-mers), more preferably at least decapeptides (10-mers), more preferably at least dodecapeptides (12-mers). The libraries for use in the present invention will preferably have been constructed into a Fuse 5 vector (Scott and Smith 1990) by the insertion of a mixture of synthetic oligonucleotides, with the random peptides fused to the minor viral coat protein pIII of the bacteriophage. Other similar systems may be utilized, as will become apparent to one skilled in the art upon reading this disclosure. Preferably, the complexity of the libraries used are at least $10^6$, more preferably at least $10^8$, and even more preferably at least $10^9$. Exemplary phage displays include those described in Barbas et al., *Proc. Natl. Acad. Sci. U.S.A.* 89:4457–4461 (1992) and Garrard et al., *Gene* 128:103–109 (1993), both of which are incorporated herein by reference.

The phage display protocol of the present invention can be modified to obtain new peptide moieties with improved HA-binding potential. For example, the incubation period in the panning procedure may be shortened to select for phage clones with fast on-rates. Alternatively, if the initial panning procedure does not produce a peptide with sufficient secondary structure (e.g., random coil) that is usually required for efficient binding, a "cystine-constrained" phage library may be utilized to identify new peptide moieties with "constrained" structure and improved binding. See e.g. S. E. Cwirla et al., *Science,* 276:1696 (1997), which is incorporated herein by reference. Biochemical characterization of Peptide 1 will also provide a platform from which one can design a second set of modified peptides with improved binding, stability, and even penetration.

The phage display technique of the invention can be performed in solution or using a solid support. For example, if the carbohydrate to be bound is associated with an antibody, the assay may take place in solution, and the carbohydrate-peptide complex purified using immunoprecipitation techniques. The technique can also be carried out using a support surface with associated carbohydrate, which result in the peptides which associate with the carbohydrate being immobilized on the support surface. The support surface for use in the phage display technique of the invention may be of any material known in the art, including flexible or rigid solid supports. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, the rigid substrates of the method of the present invention are sufficient to provide physical support and structure to the phage clones present thereon under the assay conditions in which the array is employed, particularly under high throughput handling conditions. Furthermore, when the rigid supports of the subject invention are bent, they are prone to breakage. In a preferred embodiment, the support is constructed from a rigid plastic, and more preferably the support is constructed from polystyrene.

Inhibition of HA Interaction with Other Molecules

Several groups have identified CD44 as a receptor for HA (See, e.g., Aruffo et al., *Cell,* 61:1303 (1990); Lesley et al., *Exp. Cell. Res.,* 187:224 (1990); Miyake et al., *J. Exp. Med.,* 172:69 (1990); Culty et al., *J. Cell Biol.,* 111:2765 (1990)). CD44 is a family of cell-surface glycoproteins generated by alternative splicing and post-translational modification Various isoforms of CD44 are expressed by many cell types, such as T cells and B cells, granulocytes, monocytes, macrophages, and DC, including LC. In 1996, HA-CD44 interaction was reported to mediate rolling of leukocytes over endothelial cells, one of the numerous processes that take place in leukocyte homing (See, e.g., DeGrendele et al., *J. Exp. Med.,* 111:2765 (1996); Clark et al., *J. Cell Biol,* 134:1075 (1996)). HA-CD44 interaction is now known to mediate many physiological and pathological events, including leukocyte homing, tumor metastasis, tissue development, hematopoiesis, cytokine production, T cell activation, and apoptosis.

The peptides of the present invention can be used as pharmacological agents that either inhibit or enhance HA-CD44 interaction, and thus are useful to prevent and/or treat patients with diseases mediated by this interaction. Such peptides are useful in preventing contact hypersensitivity and delayed type hypersensitivity reactions (See, e.g., Camp et al., *J. Exp. Med.,* 178–497 (1993); Verdrengh et al., *Scand. J. Immunol.,* 42:353 (1995)) and to inhibit tumor metastasis (See, e.g., Bartolazzi et al., *J. Exp. Med.,* 180:53 (1994); Guo et al., *Cancer Res.,* 54:1561 (1994); Zahalka et al., *J. Immunol.,* 154:5345 (1995)). Moreover, the peptides of the invention are useful as modulators of HA-CD44 mediated responses such as those documented in collagen-induced autoimmune arthritis models (See, e.g., Verdrengh et al., *Scand. J. Immunol.,* 42:353 (1995); Mikecz et al., *Nat. Med.,* 1:558 (1995); Zeidler et al., *Autoimmunity,* 21:245 (1995)).

Isolated peptide inhibitors of HA can be used to prevent the induction of immune reactions in the sensitization phase and to inhibit inflammatory reactions in the elicitation phase. This is based in part on the following observations: keratinocytes express relatively large amounts of cell-surface hyaluronan (HA), and the long-term Langerhans cell (LC) line XS106 exhibits significant rolling over HA-coated plates as well as over confluent keratinocyte monolayers under physiological flow conditions; XS106 cell rolling is blocked by soluble HA; and local injection of soluble HA into mouse skin inhibits almost completely LC emigration that is triggered by topical application of DNFB (See, e.g., Mohamadzadeh et al., *J. Invest. Dermatol.,* in press: (abstract) (1999)). The peptides isolated using the method of the invention are thus useful to inhibit a mechanism of DC migration, e.g. an interaction between HA (on keratinocytes) and CD44 (on activated LC).

CD44 is only one of several receptors for HA, and HA is only one of several ligands of CD44. Other molecules, including but not limited to RHAMM, aggrecan, versican, link protein, the LEC HA receptor, hyaluronection, inter-α-trypsin inhibitor-related proteins, BEHAB, CD38, CD54, and hyaluronidase (HAase), also bind HA (See, e.g., Kahn et al., *J. Orthop. Res.,* 12:612 (1994); Knudson et al., *FASEB J.,* 7:1233 (1993)). The peptides isolated may also potentiate or inhibit HA-mediated activity through these molecules, as will be apparent to one skilled in the art upon reading the present disclosure.

Therapeutic Use of Isolated Peptides

The isolated peptides of the invention can be used in a variety of applications including human and veterinary therapies, either alone or in combination with other therapeutic agents. Administration of peptide inhibitors or enhancers may be advantageous over administration of other therapeutic agents due to their lower molecular weight, which can allow the peptide to enter cells more readily than the other, higher molecular weight therapeutics such as antibodies. Thus peptide modulators of glycosaminoglycan activity will have better bioavailability than therapeutic agents having higher molecular weights.

Peptides that inhibit HA activity can be used in the treatment of diseases associated with excess hyaluron, and/or as an anti-cancer agent either alone or in combination with chemotherapeutic agents. Of particular interest is the administration of anti-HA peptides to patients suffering from stroke or a myocardial infarction (e.g., by infusion) (see, e.g., Maclean et al. 1976 *Science* 194:199–200; Opie 1980 *Am Heart J.* 100:531–52). Administration of peptide inhibitors of HA to patients suffering from myocardial infarction can facilitate a decrease in pressure upon myocardial tissues, prevent tissue necrosis, and relieve edema. Use of peptide inhibitors of HA activity in treatment of myocardial infarct patients is advantageous over use of therapeutic agents such as hyaluronidase (HAase) since the peptide's activity is specific to HA and thus will not be inhibited by heparin. Heparin is often administered during heart attacks and is a very powerful inhibitor of HAase activity of other HAase containing this EGF motif. Because the peptide inhibitors of HA are not subject to regulation by heparin, the clinician need not be concerned that co-administration of heparin with the anti-HA peptide.

Peptides that inhibit HA activity can also be used in the treatment of edema associated with brain tumors, particularly that associated with glioblastoma multiform. The edema associated with brain tumors results from the accumulation of HA in the non-cancerous portions of the brain adjacent the tumor. Administration of the HA-specific peptide inhibitor to the sites of hyaluronan accumulation (e.g., by intravenous injection or via a shunt) can relieve the edema associated with such malignancies by binding to and preventing activity of excess HA these sites. Thus, HA inhibitors can be successful in the treatment of brain tumors not only in the reduction of the tumor mass and inhibition of tumor growth and/or metastasis, but it also is useful in relieving edema associated with the malignancy.

Of particular interest is the use of HA-specific peptide inhibitors in the treatment of cancer. Isolated anti-HA peptides can be used as a chemotherapeutic agent (alone or in combination with other chemotherapeutics) in the treatment of any of a variety of cancers, particularly invasive tumors. For example, peptides of the invention can be used in the treatment of small lung cell carcinoma, squamous lung cell carcinoma, as well as cancers of the breast, ovaries or any other cancer associated with increased levels of HA. Anti-HA peptides can also be used to increase the sensitivity of tumors that are resistant to conventional chemotherapy.

HA-specific peptide inhibitors may also be used in the treatment, amelioration and/or prevention of infectious disease such as HIV infection. For example, HIV and other infectious organisms are known to bind to HA upon infection of cells. Peptides of the invention can be used to inhibit this interaction or HA-mediated activity stemming from interaction of HA with and infectious organism.

Since HA is known to be involved in migration of cells such as leukocytes, peptides that inhibit HA activity may also be useful in the treatment and/or prevention of inflammation. For example, a patient with an autoimmune disease, e.g. lupus or rheumatoid arthritis, may be treated with a composition of the invention, either systemically or locally, e.g. injection into a joint to decrease inflammation caused by arthritis. In addition, peptides of the invention may be useful to prevent autoimmune problems stemming from procedures such as bone marrow transplants, e.g. suppression of graft-versus-host disease.

The peptides of the invention may also be useful as a form of contraception, since HA is known to mediate binding of the sperm to the oocyte. Peptides that inhibit HA may inhibit binding between the sperm and the oocyte, since such binding requires HA-mediated binding, thus effectively prevent fertilization, thus effectively preventing formation of the zygote.

In some therapeutic applications of the peptide of the invention, it may be desirable to modify the peptides to provide one or more desirable characteristics. Various methods for increasing the half-life of a protein are well known in the art and include, for example, conjugation of the protein to polyethylene glycol moieties, i.e., PEGylation (see, for example, U.S. Pat. Nos. 4,179,337; 5,166,322; 5,206,344; Nucci et al., *Adv. Drug Delivery Rev.* 4:133–151 (1991); Zalipsky et al., "Polymeric Drugs and Drug Delivery Systems," ACS (1991)) conjugation of the protein to dextran (Maksimenko, *Bull. Exp. Biol. Med.* (*Russian*) 52:567–569 (1986)), and deglycosylation of the protein by treatment with endoglycosidase F (Lace et al., *Carbohydrate* (1990)).

When used in the therapeutic treatment of disease, an appropriate dosage of an anti-glycosaminoglycan, or mixture thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host.

Where the therapeutic use of the presently described peptides is contemplated, the peptides are preferably administered in a pharmaceutically acceptable carrier, via oral, intranasal, rectal, topical, intraperitoneal, intravaginal, intravenous, intramuscular, subcutaneous, intracranial, subdermal, transdermal, intratracheal methods, or the like.

Typically, but not necessarily, the preferred formulation for a given anti-glycosaminoglycan peptide is dependant on the location in a host where a given infectious organism would be expected to initially invade, or where a given infectious organism would be expected to colonize or concentrate. For example, topical infections are preferably treated or prevented by formulations designed for topical application. For example, in a preferred embodiment, the peptide is formulated in a water, ethanol, and propylene glycol base for topical administration. Alternately, where the targeted region of inflammation is internal, preparations of peptides may be provided by oral dosing. Additionally, pulmonary inflamation may be treated both parenterally and by direct application of suitably formulated forms of the peptides to the lung by inhalation therapy or intranasal administration.

Preferably, animal hosts that may be treated using the peptides of the present invention include, but are not limited to, invertebrates, vertebrates, birds, mammals such as pigs, goats, sheep, cows, dogs, cats, and particularly humans.

Pharmaceutical Compositions and Delivery

The presently described peptides may be formulated with a variety of physiological carrier molecules. The isolated peptides may also be complexed with molecules that enhance their ability to enter the target cells. Examples of such molecules include, but are not limited to, carbohydrates, polyamines, amino acids, peptides, lipids, and molecules vital to bacterial growth. For example, the peptides may be combined with a lipid, cationic lipid, or anionic lipid. The resulting peptide/lipid emulsion, or liposomal suspension may, inter alia, effectively increase the in vivo half-life of the peptide. Examples of suitable anionic lipids for use with therapeutic peptides include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol. The use of cationic, anionic, and/or neutral lipid compositions or liposomes is generally described in International Publications Nos. WO 90/14074, WO 91/16024, WO 91/17424, and U.S. Pat. No. 4,897,355, herein incorporated by reference.

By assembling the glycoaminoglycan-modulating peptides into lipid-associated structures, the peptides may be targeted to specific bacterial cell types by the incorporation of suitable targeting agents (i.e., specific antibodies or receptors) into the peptide/lipid complex.

Pharmaceutical compositions containing the peptides of the invention in admixture with a pharmaceutical carrier can be prepared according to conventional pharmaceutical compounding techniques. The carrier may take a wide variety of forms depending on the form of the preparation desired for administration, e.g., intravenous, oral, topical, aerosol (for topical or pulmonary delivery), suppository, parenteral, or spinal injection.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated and enteric-coated by standard techniques.

For parenteral application by injection, preparations may comprise an aqueous solution of a water soluble, or solubilized, and pharmaceutically acceptable form of the peptide in an appropriate saline solution. Injectable suspensions may also be prepared using appropriate liquid carriers, suspending agents, agents for adjusting the isotonicity, preserving agents, and the like. Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference. The presently described peptides should be parenterally administered at concentrations below the maximal tolerable dose (MTD) established for the particular peptide to be administered.

For topical administration, the carrier may take a wide variety of forms depending on the preparation, which may be a cream, dressing, gel, lotion, ointment, or liquid.

Aerosols can be prepared by dissolving or suspending the isolated protein preparation in a propellant such as ethyl alcohol or in propellant and solvent phases. The pharmaceutical compositions for topical or aerosol form will generally contain from about 0.01% by weight (of the peptide) to about 40% by weight, preferably about 0.02% to about 10% by weight, and more preferably about 0.05% to about 5% by weight depending on the particular form employed.

Suppositories are prepared by mixing the peptide with a lipid vehicle such as theobroma oil, cacao butter, glycerin, gelatin, or polyoxyethylene glycols.

The presently described isolated peptides may be administered to the body by virtually any means used to administer conventional antibiotics. A variety of delivery systems are well known in the art for delivering bioactive compounds to an animal. These systems include, but are not limited to, intravenous or intra-muscular or intra-tracheal injection, nasal spray, aerosols for inhalation, and oral or suppository administration. The specific delivery system used depends on the location of the area to be treated, and it is well within the skill of one in the art to determine the location and to select an appropriate delivery system.

Suitable examples of sustained-release preparations include semipermeable matrices of solid hydrophobic polymers containing the peptide, which matrices are in the form of shaped articles, e.g., films, or microcapsules. Examples of sustained-release matrices include polyesters, hydrogels (e.g., poly(2-hydroxyethyl-methacrylate) as described by Langer et al. (1981) J. Biomed. Mater. Res. 15:167–277 and Langer (1982) Chem. Tech. 12:98–105, or poly(vinyl alcohol)), polylactides (U.S. Pat. No. 3,773,919, EP 58,481), copolymers of L-glutamic acid and gamma ethyl-L-glutamate (Sidman et al. (1983) Biopolymers 22:547–556), non-degradable ethylene-vinyl acetate (Langer et al. (1981) supra) degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

Compositions inhibiting glycosaminoglycans activity also may be entrapped in microcapsules prepared, for example, by coacervation techniques or by interfacial polymerization (for example, hydroxymethylcellulose or gelatin-microcapsules and poly-(methylmethacylate]microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

While polymers such as ethylene-vinyl acetate and lactic acid-glycolic acid enable release of molecules for over 100 days, certain hydrogels release molecules for shorter time periods. When encapsulated molecules remain in the body for a long time, they may denature or aggregate as a result of exposure to moisture at 37° C., resulting in a loss of biological activity and possible changes in immunogenicity. Rational strategies can be devised for stabilization depending on the mechanism involved, e.g., using appropriate additives, and developing specific polymer matrix compositions.

Sustained-release compositions also include liposomally entrapped peptides. Liposomes containing compositions of the invention are prepared by methods known per se: DE 3,218,121; Epstein et al. (1985) Proc. Natl. Acad. Sci. USA 82:3688–3692; Hwang et al. (1980) Proc. Natl. Acad. Sci. USA 77:4030–4034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol % cholesterol, the selected proportion being adjusted for the optimal therapy. A specific example of a suitable sustained-release formulation is in EP 647,449.

An effective amount of composition to be employed therapeutically will depend, for example, upon the therapeutic objectives, the route of administration, and the condition of the patient. Accordingly, it will be necessary for the clinician to titer the dosage and modify the route of administration as required to obtain the optimal therapeutic effect. A typical daily dosage of a molecule used alone might range from about 1 μg/kg to up to 100 mg/kg of patient body weight or more per day, depending on the factors mentioned above, preferably about 10 μg/kg/day to 50 mg/kg/day.

Nucleotide sequences, including antisense sequences, can be therapeutically administered by various techniques known to those skilled in the art. Delivery of nucleotide sequences encoding modulators of carbohydrate activity can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Cosmetic Use of Isolated Peptides

The isolated peptides of the invention may be used in cosmetic products such as lotions, creams, topical solutions. For example, the peptides of the invention may be used in topical lotions as an antiinflamatory agent to reduce epidermal swelling. Thus, the peptides of the invention may be used with any known cosmetic preparation where such a use may be beneficial, including but not limited to lotions, foundations, creams, gels, soaps and the like. The peptides are present in an amount sufficient to have an antibacterial effect, and preferably between 0.25 wt % and 10.0 wt %, more preferably between 0.5 wt % and 5.0 wt %.

The cosmetic composition of the invention may contain any of a number of additives that are themselves active ingredients, such as a glycolic or alpha-hydroxy acids, vitamin A palmitate (retinyl palmitate) and/or vitamin E acetate (tocopheryl acetate). Each of these is preferably present in an amount from about 0.5 wt. % to about 5 wt %. In addition, a UV absorbing or blocking material, such as PABA, may be used.

Other compounds may also be added to have additional moisturizing effects and to improve the consistency of the composition. Examples of such compounds include, but are not limited to: certyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. See, e.g., U.S. Pat. Nos. 5,153,230 and 4,421,769, which are both incorporated herein by reference. If it is desirable for the composition to have additional cleaning effects, chemicals such as sodium laurel sulfate or a metal salt of a carboxylic acid may be added.

A wide variety of nonvolatile emollients are useful herein, nonlimiting examples of which are listed in *McCutcheon's, Vol. 2 Functional Materials,* North American Edition, (1992), pp. 137–168, which is incorporated herein by reference in its entirety, and *CTFA Cosmetic Ingredient Handbook,* Second Edition (1992) which lists Skin-Conditioning Agents at pp. 572–575 and Skin Protectants at p. 580, which is also incorporated herein by reference in its entirety.

Among the nonvolatile emollient materials useful herein especially preferred are silicones, hydrocarbons, esters and mixtures thereof.

Examples of silicone emollients include polyalkylsiloxanes, cyclic polyalkylsiloxanes, and polyalkylarylsiloxanes. The polyalkylsiloxanes useful herein include, for example, polyalkylsiloxanes with viscosities of from about 0.5 to about 100,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer from 0 to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful as emollients herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Cyclic polyalkylsiloxanes useful herein include those corresponding to the general chemical formula $[SiR_2O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes and a boiling point of 172° C., which primarily contains the cyclomethicone tetramer (i.e., n=4), Dow Corning® 344 fluid having a viscosity of 2.5 centistokes and a boiling point of 178° C., which primarily contains the cyclomethicone pentamer (i.e., n=5), Dow Corning® 245 fluid having a viscosity of 4.2 centistokes and a boiling point of 205° C., which primarily contains a mixture of the cyclomethicone tetramer and pentamer (i.e., n=4 and 5), and Dow Corning® 345 fluid having a viscosity of 4.5 centistokes and a boiling point of 217° C., which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_3)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g., Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Hydrocarbons useful herein include straight and branched chain hydrocarbons having from about 10 to about 30 carbon atoms, more preferably from about 12 to about 24 carbon atoms, and most preferably from about 16 to about 22 carbon atoms. Nonlimiting examples of these hydrocarbon materials include dodecane, squalane, cholesterol, hydrogenated polyisobutylene, docosane (i.e., a $C_{22}$ hydrocarbon), hexadecane, isohexadecane (a commercially available hydrocarbon sold as Permethyl® 101A by Presperse, South Plainsfield, N.J.). Other hydrocarbon materials useful herein include paraffins and mineral oils such as USP light mineral oil (e.g., Klearol® available from Witco Corp., Melrose Park, Ill.) and USP heavy mineral oil (e.g., Klearol® available from Witco Corp., Melrose Park, Ill.).

Also useful as nonvolatile emollients are esters, including esters of monofunctional and difunctional fatty acids that have been esterified with alcohols and polyols (i.e., alcohols having two or more hydroxy groups). A wide variety of esters are useful herein, with long chain esters of long chain fatty acids being preferred (i.e., C10–40 fatty acids esterified with C10–40 fatty alcohols). Nonlimiting examples of esters useful herein include those selected from the group consisting of diisopropyl adipate, isopropyl myristate, isopropyl palmitate, myristyl propionate, ethylene glycol distearate, 2-ethylhexyl palmitate, isodecyl neopentanoate $C_{12-15}$ alcohols benzoate, di-2-ethylhexyl maleate, cetyl palmitate, myristyl myristate, stearyl stearate, cetyl stearate, behenyl behenrate, and mixtures thereof.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Isolation of HA-Specific Peptides

A phage library was constructed consisting of random 12-mer peptides fused to a minor coat protein (pIII) of the M13 phage. The estimated complexity of the library was determined to be about $10^9$. Phage clones ($10^{11}$ pfu) were then incubated on polystyrene tissue culture plates that had been coated with HA and counter-coated with BSA.

The 35 mm tissue culture plates were coated overnight at 4° C. with 2.5 mg/ml HA in PBS and then washed three times with PBS (2 min/wash). To block the non-specific binding sites, the plate was then counter-coated with 1% heat-denatured BSA in PBS for 30 min at room temperature. After three additional washes with PBS, the phage ($10^{11}$ pfu) suspended in PBS was added to the HA-coated/BSA-counter coated plate. After 60 min incubation at room temperature, the unbound phage clones were removed by extensive wash; 10 times with PBS alone and 10 additional times with 0.1% Tween20 in PBS for 30 seconds each wash. The plates were then treated for 60 minutes at 37° C. with 30 units/ml of hyaluronidase (derived from bovine testis) in sodium phosphate (pH 6.0) with 0.1% BSA. This effectively eluted only those phage clones that had bound specifically to the HA substrate and not to polystyrene surfaces or BSA.

The phage clones that had been released by this treatment were collected with a pipette and amplified for the next round of panning. Phage clones were expanded in E. coli and incubated on tissue culture plates that had been coated with chondroitin sulfate (CSA), a control glycosaminoglycan which also binds to CD44. Clones that did not bind to the CSA substrate were subjected to a second cycle of selection on the HA substrate. The efficacy of the procedure is dependent in large part of the HAase treatment at the elution step.

After four cycles of selection, 19 independent phage clones that had bound to the HA substrate were isolated and sequenced. 13 of the 19 clones expressed an identical peptide motif of GAHWQFNALTVR (designated Peptide 1; SEQ ID NO:1). Two motifs were identified (Peptides 2 and 3; SEQ ID NO:2 and SEQ ID NO:3) that were expressed by multiple phage clones and two (Peptides 4 and 5; SEQ ID NO:4 and SEQ ID NO:5) that were expressed by single clones. In sum, despite a theoretical complexity of $10^9$, the majority (13/19) of phage clones selected an identical peptide motif (i.e., Peptide 1).

None of the isolated peptides contained "diagnostic" sequences that are commonly found in peptides that bind non-specifically to the polystyrene surface. In addition, none of the identified peptides showed significant (>25%) sequence identities to the known HA-binding domain sequences of CD44, RHAMM, and link protein. B. Yang et al., *EMBO J.* 13:286 (1994). Although a consensus motif conserved among the aforementioned three HA receptors—B(X)$_7$B, where B represents a basic amino acid residue and X represents any non-acidic amino acid residue—was detected in Peptides 1, 3, and 4, it appeared that this motif was not a factor in the ability of these peptides to bind to HA. The residues that were apparently critical for binding were aliphatic or polar aliphatic residues at positions 4, 5 and 6 and again at 9, 10 and 11, thus defining a peptide binding motif of ZZZXZZZ from residues 4–11 of the peptide. In contrast, amino acids at positions 3, 7 and 12 appear to be dispensable, and position 1 appears to be less important than the other 6.

Example 2

Binding Efficacy of the Isolated HA-Specific Peptides

Each of the four isolated HA-binding peptides (Peptides 1 through 4) and a "random" control peptide (selected from phage clones which failed to bind to HA) were synthesized to examine their specificity to HA. The random peptide sequence was SATPASAPYPLAGGGS (SEQ ID NO:6). The peptides tested also had a spacer sequence of GGgS (SEQ ID NO:10) at the carboxy terminus of the peptide.

Phage clones expressing each of the HA-binding peptides were incubated for two hours on HA-coated polystyrene plates. After extensive washing, phage that were still bound to the HA substrate were eluted by HAase treatment and the isolated phage were titrated to determine the extent of each peptide's binding to HA. Peptide 1 showed the most significant binding to both HA-coated plates and native HA molecules expressed on keratinocytes.

Figure 1:
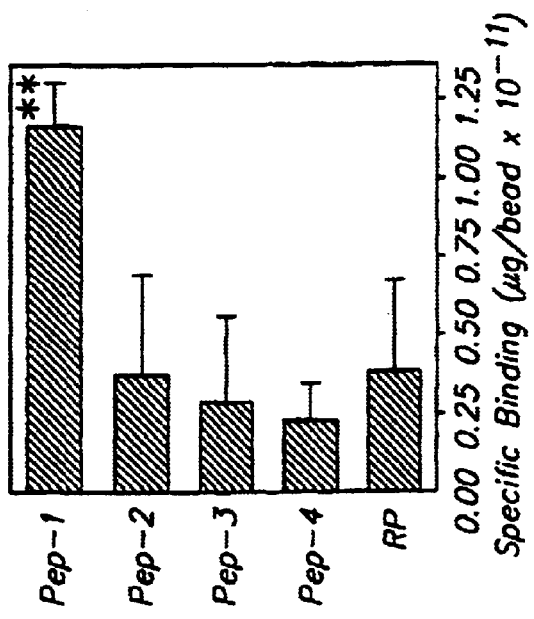
FIG. 1 is a bar graph illustrating the binding specificity of each of the four isolated peptides and a random peptide (RP) to HA-coated beads. The asterisks indicate statistically significant differences ($p<0.01$).

Each of the indicated 12-mer peptides was labeled with $^{125}$I and tested at 50 µg/ml for the binding to HA-coated beads. The peptides were radiolabeld at the N-terminus using the Bolton-Hunter reagent and incubated for 2 hours at 4° C. Following incubation, the beads were washed three times and the levels of binding detected. Again, Peptide 1 was found to display specific binding to the HA-coated beads (FIG. 1).

Figure 3:
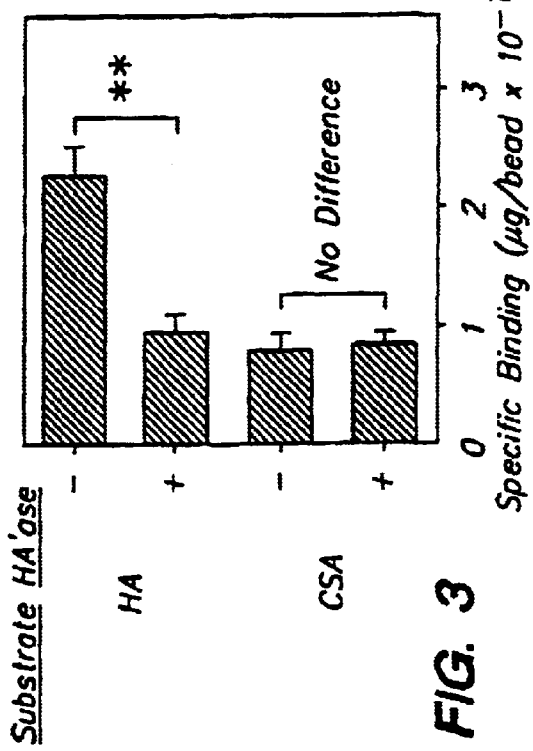
FIG. 3 is a bar graph illustrating the relative binding of each isolated Peptide 1 to HA and CSA. Brackets indicate comparisons evaluated by the students 2-tailed t-test. The asterisks indicate statistically significant differences ($p<0.01$).

$^{125}$I-labeled Peptide 1 was then tested at different concentrations for the binding to HA-coated beads. The specific binding of the peptide to the beads was shown to increase with the concentration of peptide used (FIG. 2). The specificity of Peptide 1 for HA, rather than for any glycosaminoglycan, was determined by incubating the $^{125}$I-labeled Peptide 1 with HA-coated or CSA-coated beads in the presence or absence of HAase pretreatment. Peptide 1 showed a much lower level of binding to CSA, both with and without HAase pretreatment (FIG. 3). Levels of binding were in fact the same between the HAase treated CSA coated beads and the untreated CSA beads. Binding of Peptide 1 to the HA coated beads was significantly increased over the HA coated beads pretreated with HAase, indicating that the presence of intact HA is necessary for the specific binding.

Figure 4:
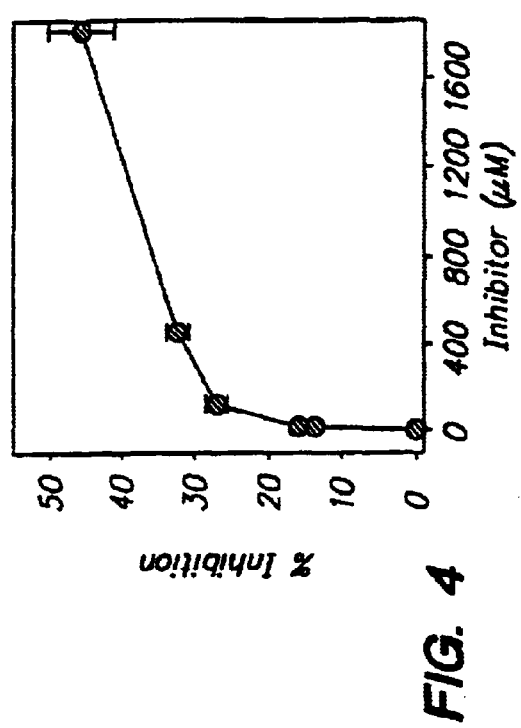
FIG. 4 is a line graph depicting the inhibition of radiolabeled Peptide 1 by unlabeled Peptide 1. Data shown are mean±SD (n=3) of $OD_{405}$.

Unlabeled Peptide 1 was tested for its ability to inhibit binding of $^{125}$I-labeled Peptide 1. HA-coated beads were first incubated with the indicated concentrations of non-labeled Peptide 1 (0 to 1780 $\mu$M). One hour later, $^{125}$I-labeled Peptide 1 (50 $\mu$g/ml) was added to the beads and tested for binding. The non-labeled Peptide 1 effectively inhibited the ability of the labeled peptide in a concentration-dependent manner (FIG. 4).

Example 3

Binding of Peptide 1 to Native HA Molecule on Endothelial Cells

Biotinylated Peptide 1 through Peptide 4 were tested at 62 $\mu$M for the binding to SVEC 10–40 endothelial cells. As a control, cells were incubated with biotinylated RP. After washing to remove unbound peptides, the cells were incubated with streptavidin-FITC and subjected to FACS analyses (FIG. 5). Peptide 1 displayed a much higher affinity to the endothelial cells than either RP or Peptides 2–4.

SVEC cells were then treated with hyaluronidase (330 U/ml) or mock-treated (open histogram with broken lines) prior to incubation with biotinylated Peptide 1 (62 $\mu$M), or biotinylated RP. The binding efficiency of Peptide 1 was dramatically reduced in the HAase treated cells as compared to both the mock treated cells (FIG. 6).

Example 4

Inhibition of Soluble HA Binding to Leukocyte Surfaces by Peptide 1

Figure 7:
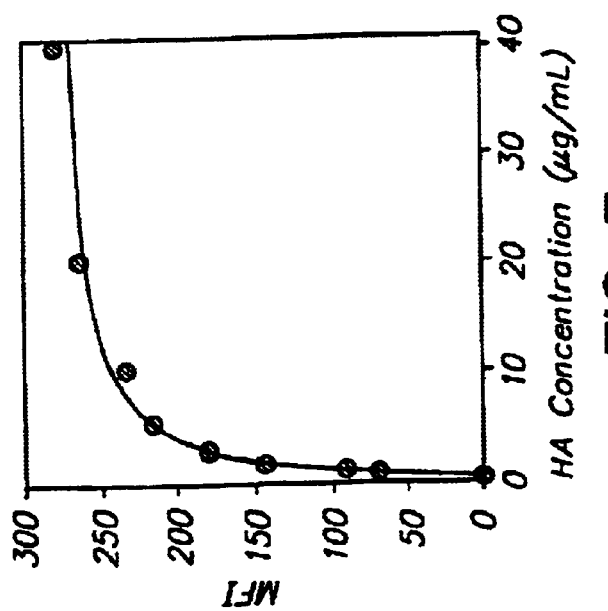
FIG. 7 is a line graph illustrating the ability of Peptide 1 to inhibit HA binding.

To examine the competitive binding ability of Peptide 1, various concentrations of FITC-conjugated HA were incubated at the indicated concentrations with BW5147 thymoma cells as shown in FIG. 7. Cells were incubated with Peptide 1 for one hour on ice. After incubation, cells were washed three times with Dulbecco's PBS (Sigma) with 5% fetal calf serum to remove the unbound FITC-conjugated HA. The cells were then analyzed by FACS to determine mean fluorescent intensities (MFI). Data were plotted linearly and evaluated with a hyperbolic fit. Saturation was determined to be at 1.40 $\mu$g/ml and saturation was at 279.40 $\mu$g/ml.

Figure 8:
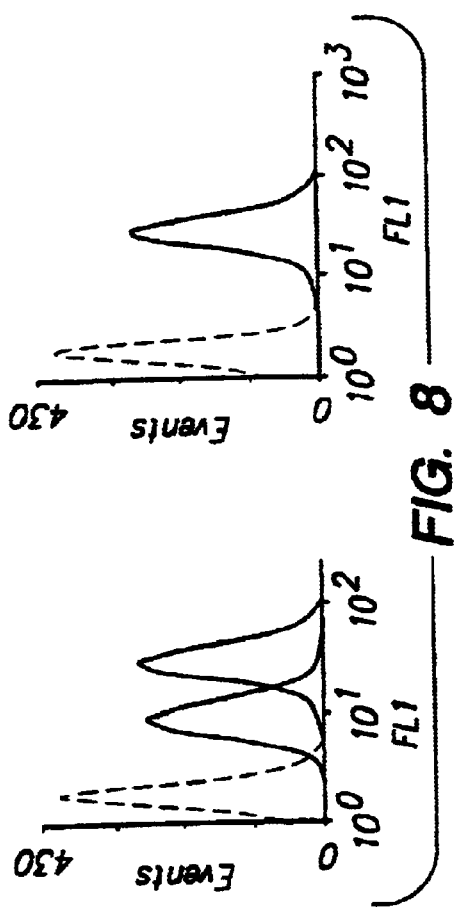
FIGS. 8a and 8b are histograms illustrating FITC-HA binding to BW5147 cells before or after pretreatment with either Peptide 1 or RP (500 μg/ml).

FITC-labeled HA was tested for the binding to BW5147 cells either before (FIG. 8, open histogram) or following (FIG. 8, shaded histogram) pretreatment with Peptide 1. 1 $\mu$g/ml FITC-HA was incubated with BW5147 cells and either Peptide 1 (FIG. 8a) or RP (FIG. 8b), both at 500 $\mu$g/ml. Hisotgrams with broken lines represent the level of autofluorescence after incubation with PBS alone. Binding of HA to cells pretreated with Peptide 1 decreased significantly compared to cells treated with Peptide 1 following HA binding (FIG. 8a). In contrast, cells treated with RP showed no difference between pretreatment and treatment following HA binding (FIG. 8b).

Figure 9:
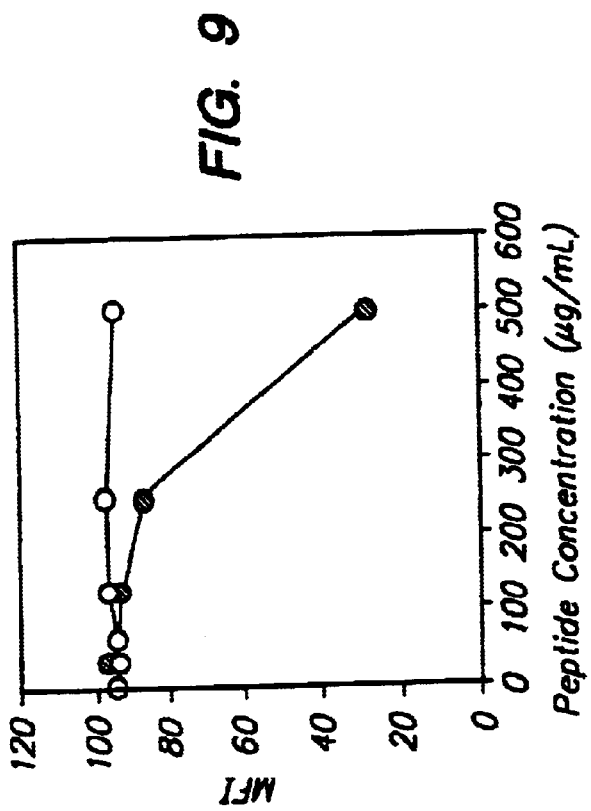
FIG. 9 illustrates binding of Peptide 1 (closed circles) or RP (open circles) to BW5147 cells. The data shown are the MFI as measured by FACS.

The ability of Peptide 1 or RP to inhibit subsequent HA binding to BW5147 cells was also tested with different concentrations of Peptide 1 (FIG. 9). The cells treated with RP showed no difference in HA binding with increased RP binding, whereas treatment with Peptide 1 caused a decrease in HA binding in a concentration-dependent manner.

Example 5

Inhibition of CD44-Dependent Leukocyte Adhesion to HA-Coated Substrates Using Peptide 1

Figure 10:
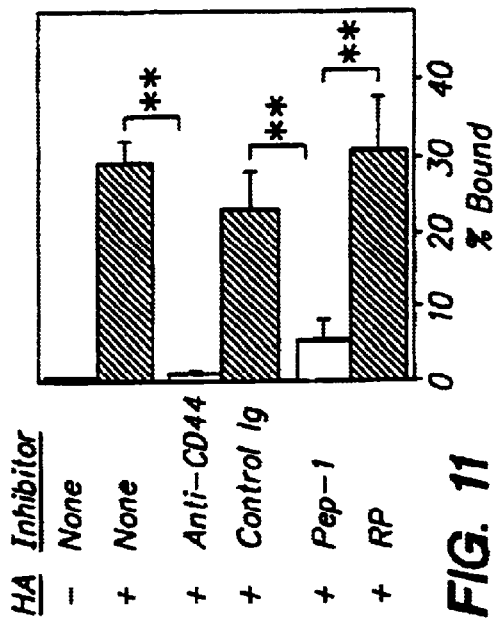
FIG. 10 is a line graph illustrating the binding of BW5147 to the indicated concentrations of HA.

Peptide 1 was then tested for its ability to block CD44-dependent leukocyte adhesion of BW5147 cells to HA-coated substrates. $^{35}$S-labeled BW5147 cells were incubated for 30 min at room temperature in culture wells that had been coated with various concentrations of HA (See FIG. 10). After three washes in Dulbecco's PBS (Sigma) to remove unbound cells, the bound cells were lysed in 1% SDS and the radioactivity of each well measured to determine the number of cells adhered to each well. The data shown in FIG. 10 are the means±s.d. of % binding from triplicate samples. The amount of radioactivity detected increased with the increase in HA concentration.

Figure 11:
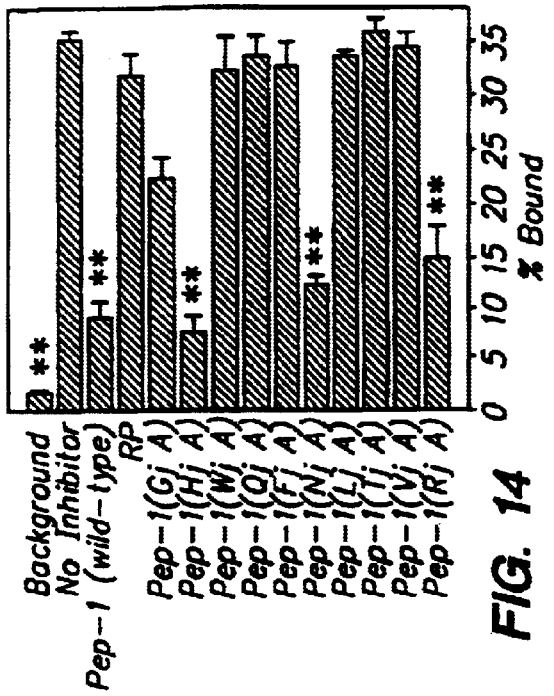
FIG. 11 is a bar graph illustrating binding of BW5147 cells to the HA-coated plates after pretreatment of the cells with 70 μg/ml of anti-CD44 mAb or control IgG, or after pretreatment of the substrate with Peptide 1 or RP.
Figure 12:
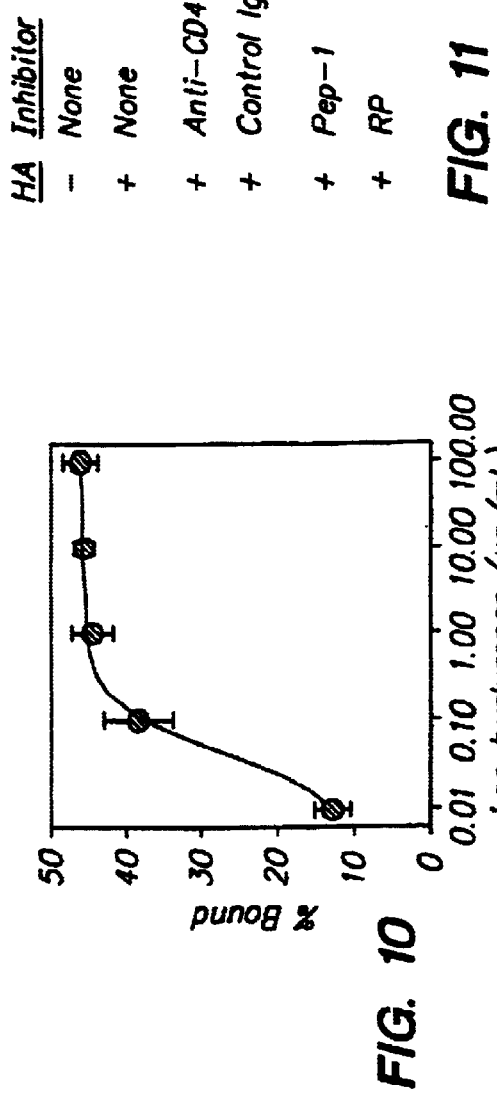
FIG. 12 is a line graph illustrating the binding of BW5147 cells to HA-coated wells pretreated with the indicated concentrations of Peptide 1 (closed circles) or RP (open circles).

Binding of $^{35}$S-labeled BW5147 cells to the HA-coated wells (0.1 $\mu$g/ml) was then tested after pretreatment of the cells with 1) 70 $\mu$g/ml of anti-CD44 mAb (KM81) or control IgG, or 2) after pretreatment of the substrate with Peptide 1 or RP, each at 250 $\mu$g/ml (FIG. 11). The cells incubated with either the CD-44 antibody or with Peptide 1 displayed reduced binding compared to the IgG and RP controls, respectively.

Figure 13:
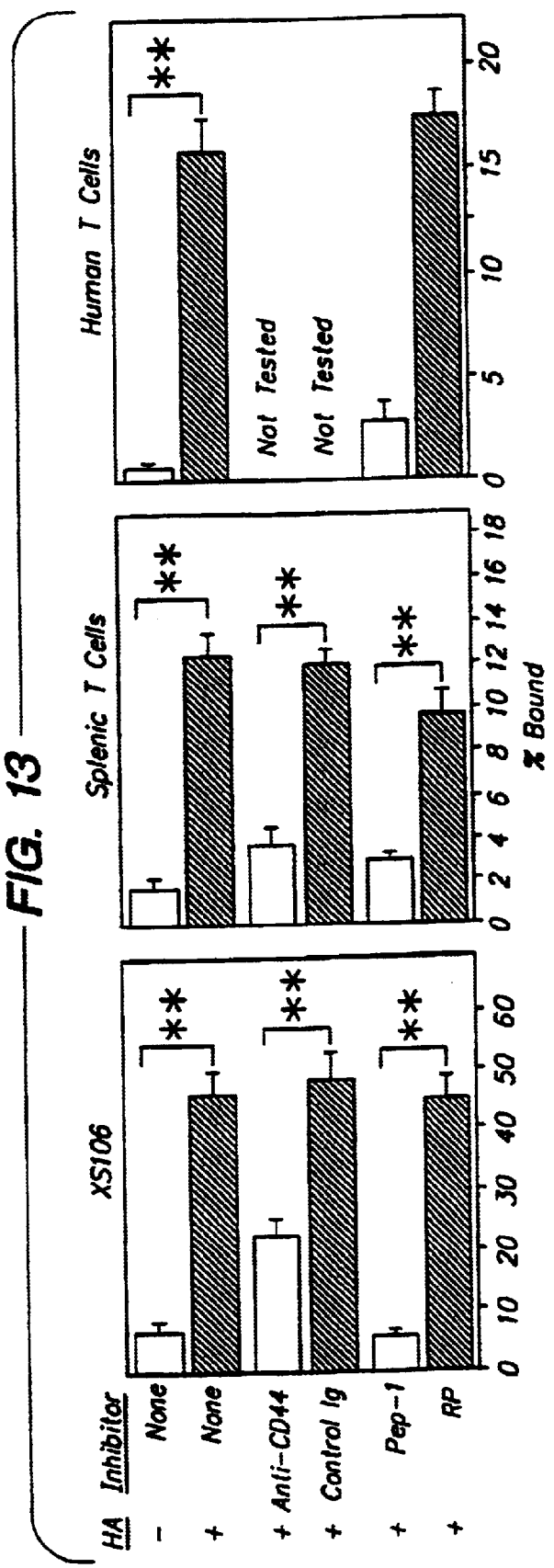
FIG. 13 is a series of bar graphs illustrating the ability of Peptide 1 to inhibit binding of HA to murine splenic T cells, human peripheral blood T cells, or murine Langerhans cells.
Figure 15:
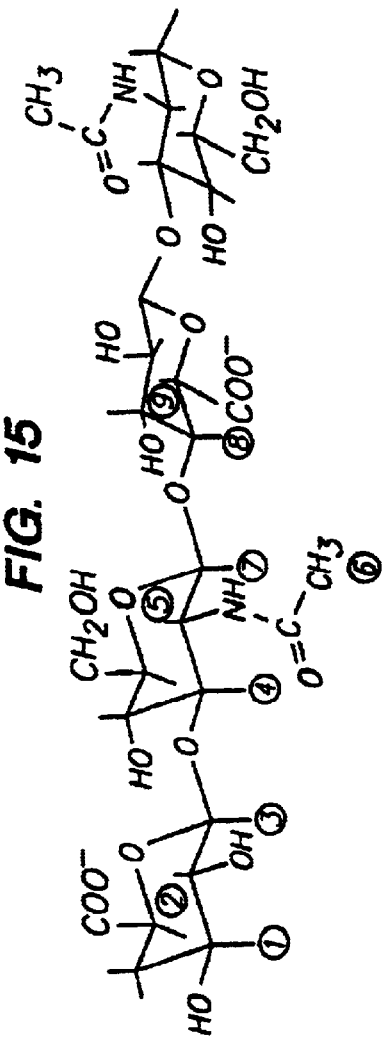
FIG. 15 illustrates the secondary structure of an HA tetrasaccharide.

Murine splenic T cells, human peripheral blood T cells, or murine Langerhans cell line XS106 were labeled with $^{35}$S and tested for the adhesion to the HA-coated plates in the presence or absence of the indicated pretreatment (FIG. 13). As shown, cells pretreated with Peptide 1 displayed a significantly decreased level of binding in all three cell types. All the data in each panel represent at least two independent experiments, showing the means±s.d. of % binding from triplicate samples. Brackets indicate groups compared by the students 2-tailed t-test. All comparisons were by the students 2-tailed t-test relative to cellular adhesion with no inhibitor.

Example 6

Determination of Residues Involved in HA Binding

Figure 14:
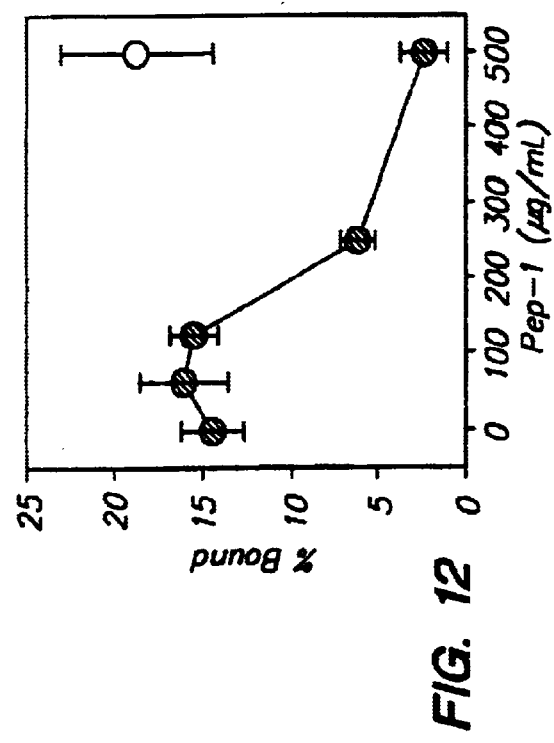
FIG. 14 is a bar graph showing the individual amino acids within the Peptide 1 sequence determined to be important by Ala scanning mutagenesis.

To determine the residues critical for Peptide 1 binding to HA, individual amino acids within the Peptide 1 sequence were replaced with Alanine by scanning mutagenesis. Wild-type Peptide 1 or each of the Alanine mutants of Peptide 1 were tested at 250 $\mu$g/ml for the impact on the adhesion of $^{35}$S-labeled BW5147 cells on HA-coated wells (FIG. 14). Results from Ala scanning mutagenesis indicate that polar aliphatic and non-polar residues are required for Peptide 1 binding to HA. All the data in each panel represent at least two independent experiments, showing the means±s.d. of % binding from triplicate samples. Brackets indicate groups compared by the students 2-tailed t-test. All comparisons were by the students 2-tailed t-test relative to cellular adhesion with no inhibitor. Interestingly, one face of the HA molecule is relatively non-polar (as indicated by the numbered —CH groups) while the other face is relatively polar (FIG. 14). Therefore, Peptide 1 may interact with polar and non-polar faces of HA.

Example 7

Impact of Peptide 1 on Hapten-triggered Langerhans Cell Migration

It had been previously observed that local injection of soluble HA into mouse skin inhibits hapten-triggered emigration of Langerhans cell (LC) from the epidermis (Mohamadzadeh et al., *J. Invest. Dermatol.*, in press: (abstract) (1999)). Thus, it was of particular interest to determine whether Peptide 1 would block LC migration.

Peptide 1 was shown to inhibit the biological function of HA in its role of mediating the migration of Langerhans cells. BALB/c mice (5 mice/group) received two subcutaneous injections (40 µl/injection) of the indicated peptide preparation (1 mg/ml in 2% DMSO) Five mice were injected per group, and each set of mice received two injections into both ears, one 24 hours before and one 1 hour before topical application of 0.5% 1-fluoro-2,4-dinitrobenzene (DNFB, Sigma Chem. Corp.) The DNFB was applied to the right ear of each mouse, and the vehicle carrier, which is comprised of olive oil and acetone was applied to the left ear as a negative control.

Figure 16:
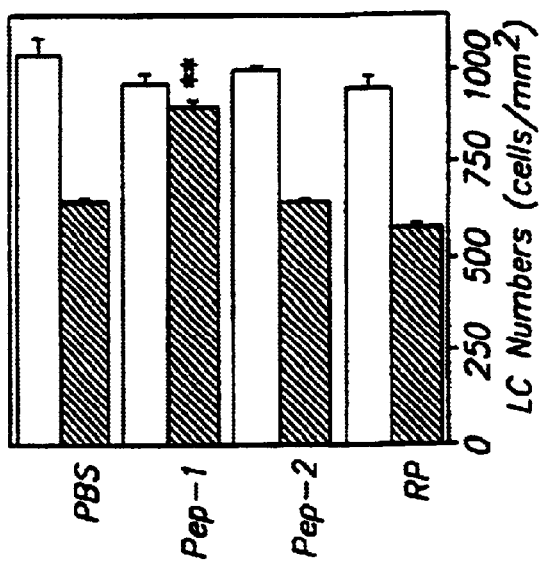
FIG. 16 is a bar graph illustrating the impact of Peptide 1 on hapten-triggered LC migration

Mice were sacrificed 24 hours after DNFB application, and the ear skin samples were harvested. Epidermal sheets were prepared from each ear skin sample, stained with FITC-conjugated anti-Ia monoclonal antibody, and examined for the number of LC (FIG. 16). In the PBS-injected control groups, DNFB application reduced the number of LC substantially and caused morphological changes compared to the PBS control group without DNFB application. In contrast, DNFB application in the Peptide 1-injected subjects induced morphological changes without significantly affecting the number of LC.

These observations were confirmed by counting the number of Ia-positive LC using fluorescence microscopy. As shown in FIG. 16, DNFB painting in untreated mice induced a 50% reduction in surface LC densities. Injection of Peptide 1 and soluble HA almost completely inhibited the DNFB-mediated LC reduction, whereas neither caused an effect in the untreated mice.

Histological examination of ear specimens harvested from these animals revealed that the extent of DNFB-induced leukocyte infiltration was markedly diminished in the Peptide 1-injected sites. Importantly, Peptide 1 inhibited the skin-directed migration of both neutrophils and T cells, with the implication that Peptide 1 can be used to block the emigration of tissue-resident leukocytes (e.g. LC in skin) as well as the immigration of inflammatory leukocytes into the inflamed tissue. These results suggest that the HA-inhibitors can be used to inhibit cutaneous immune reactions in the elicitation phase.

Figure 17:
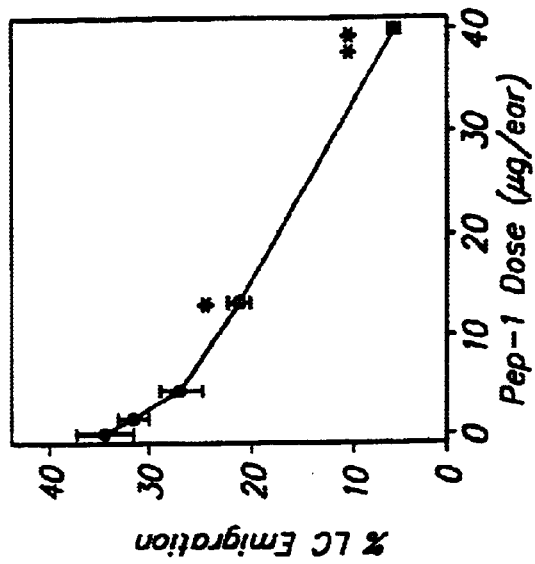
FIG. 17 is a line graph illustrating the concentration-dependent effect of Peptide 1 on LC emigration.

To determine the effect of Peptide 1 on LC emigration, a set of 5 BALB/c mice received a single 40 µl subcutaneous injection of Peptide 1 at various concentrations 24 hr before DNFB application. The percent of LC emigration decreased dramatically with an increased concentration of Peptide 1, as can be seen in FIG. 17). The data shown in FIG. 17 are the surface densities of epidermal Langerhans cells as determined at 24 hr after DNFB painting. Data shown are the means±s.e.m. from 5 samples, and statistically significant differences compared to the control group receiving no Peptide 1 are indicated with asterisks (* $p<0.05$; ** $p<0.01$) as evaluated by the students 2-tailed t-test.

Figure 18:
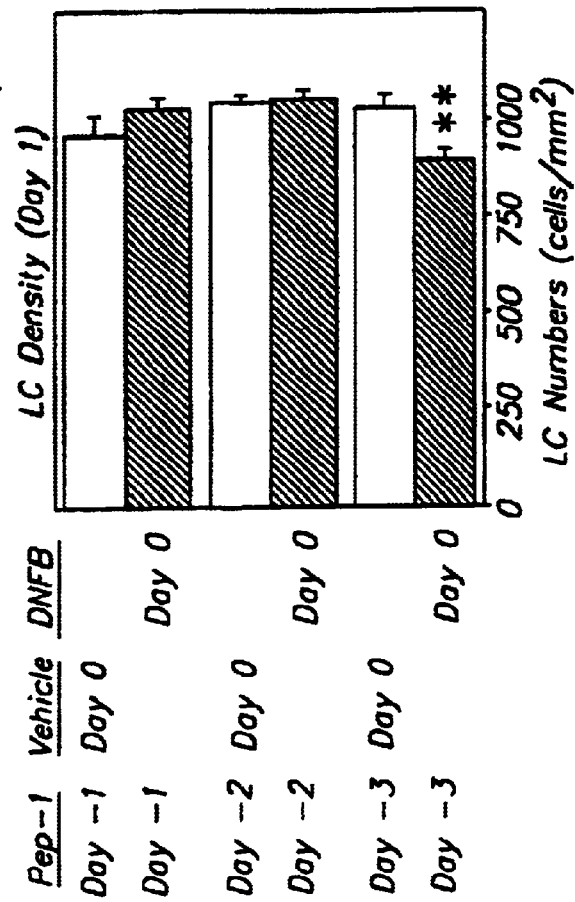
FIG. 18 is a bar graph illustrating the effect on LC density with administration of Peptide 1 at 1, 2 or 3 days before DNFB application.

Peptide 1 (40 µg/ear) was injected then injected subcutaneously into both ears of BALB/c mice at 3, 2, or 1 days before topical application of 0.5% DNFB (left ears) or vehicle alone (right ears). Twenty-four hours after DNFB painting, mice were sacrificed and examined for Langerhans cell densities (FIG. 18). The mice having Peptide 1 injected 3 days before DNFB application displayed a decreased LC density.

Data shown are the means±s.e.m. from 5 samples. DNFB treated ears were compared by ANOVA and statistically significant differences are indicated with asterisks (** $p<0.01$).

This result supports the hypothesis that HA expressed on epidermal keratinocytes serves as a physiological ligand of CD44 expressed on activated LC, thereby mediating LC emigration from the epidermis. Peptide 1 appears to block the HA ligand, as shown in the LC emigration and density studies.

Example 8

Impact of Peptide 1 on the Expression of Contact Hypersensitivity Responses As an initial step in testing the "therapeutic" potential of our peptide inhibitors, ear swelling responses to DNFB (in sensitized animals) were examined.

BALB/c mice were sensitized by topical application of 0.5% DNFB onto shaved abdominal skin and challenged 5 days later by application of 0.2% DNFB onto right ears. Left ears were painted with vehicle alone. Five mice of each group received subcutaneous injections (40 µl/injection) of Peptide 1 or 2, random control Peptide (500 µM), or soluble HA (1 mg/ml) into both ears 24 and 1 hour prior to challenge. Swelling was measured 48 hours after challenge.

Ear swelling responses were inhibited significantly by injection of Peptide 1 (or soluble HA). See FIG. 19. No inhibitory activity was observed with Peptide 2, random peptide control, or PBS alone. Swelling was measured as the change in thickness between the left and right ears. Values were compared by ANOVA. Asterisks indicate statistically significant differences (**$p<0.01$).

Histological samples harvested from the above experiments were submitted for H&E staining and examined by a third individual for the ear thickness and the number of skin-infiltrating leukocytes under a microscope. The mice treated with Peptide 1 displayed a significantly decreased ear thickness and a much lower rate of leukocyte infiltration than did the mice treated with Peptide 2, RP or PBS (FIG. 20). Brackets indicate groups compared by the students 2-tailed t-test (**$p<0.01$).

The difference in prophylactic and therapeutic response of the mice to DNFB with Peptide 1 or RP was also measured. BALB/c mice were painted on both ears with 0.5% DNFB on day 0 and with 0.2% DNFB on days 2, 4, and 6 (FIG. 21, as indicated by open arrows). Peptide 1 (closed circles) or RP (open circles) was injected subcutaneously in the left and right ears, respectively, at specific indicated time points. As can be seen in FIG. 21, mice treated with Peptide 1 displayed a significant decrease in the swelling response compared to mice treated with RP in the experiments simulating prophylactic and therapeutic uses.

The data shown are representative of two independent experiments, showing the means±s.e.m. of ear swelling responses (compared to the baseline thickness before DNFB application). Statistically significant difference between the Peptide 1 group and the RP group are shown with asterisks (* $p<0.05$; ** $p<0.01$).

Example 9

Impact of Peptide 1 on the Sensitization Phase of Contact Hypersensitivity Responses The activity of Peptide 1 in the sensitization phase of contact hypersensitivity was examined.

Figure 22:
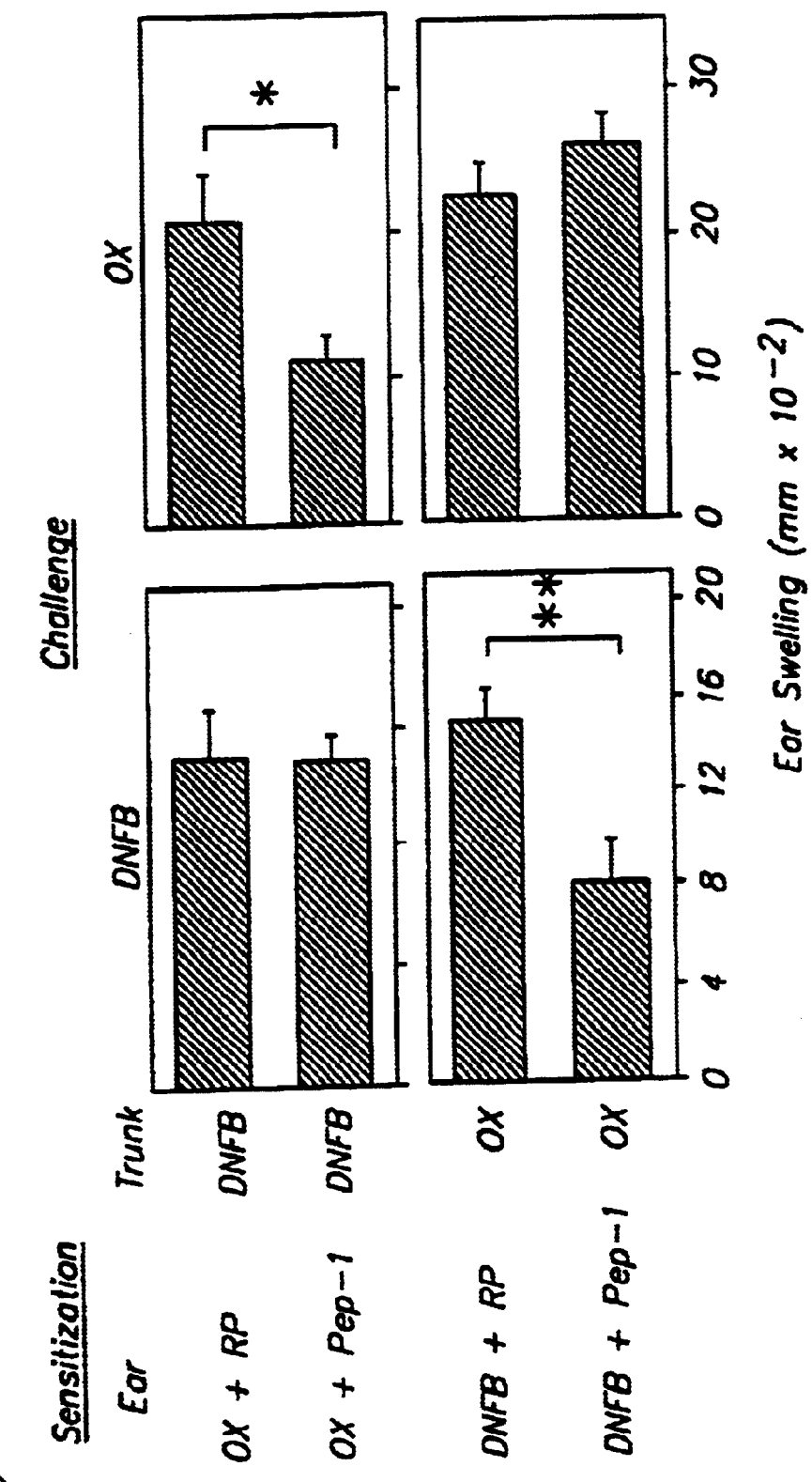
FIG. 22 is a bar graph illustrating the impact of Peptide 1 on the sensitization phase of contact hypersensitivity responses using either DNFB or oxazolone (OX).

BALB/c mice (10 mice/group) received subcutaneous injections of either Peptide 1 or RP (40 μg/ear/injection) 24 hr and 1 hr before sensitization on the left ear. The same mice were subsequently sensitized by topical application of 0.5% DNFB and 1.25% oxazolone (OX) on the indicated skin sites, either on the left ear or on shaved abdominal skin. The mice were challenged 7 days later on the right ear with 0.2% DNFB or 0.5% OX as indicated, and ear swelling measured (FIG. 22). The sensitization of either DNFB or OX on the trunk appeared to have little effect on the level of sensitivity of the mice to a challenge on the ear. The sensitization of the ear, however, decreased ear swelling following a subsequent challenge for both DNFB and OX. Thus, the use of Peptide 1 appears to decrease sensitivity to challenge in a localized manner.

Figure 23:
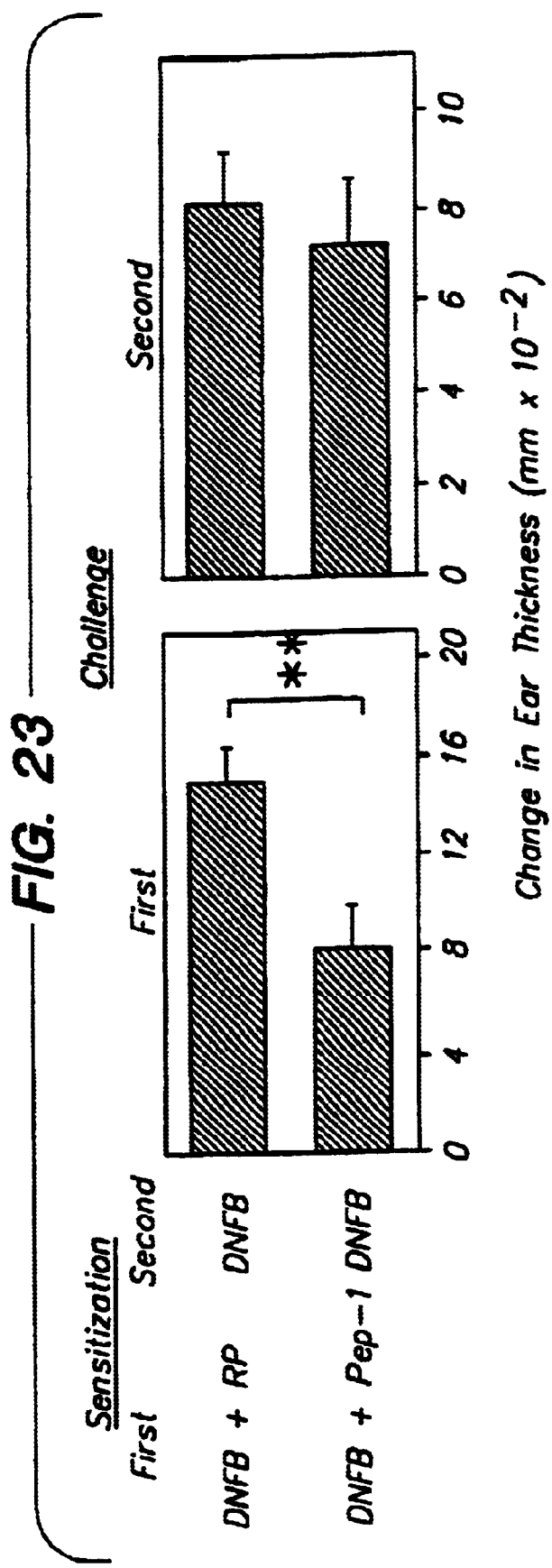
FIG. 23 is a bar graph illustrating the differences in sensitization between a first and second challenge with administration of Peptide 1 or RP.

The mice that had received Peptide 1 or RP injections and DNFB sensitization on the left ears were re-sensitized by topical application of 0.5% DNFB on the trunk on day 7, and re-challenged with 0.2% DNFB on day 14. Peptide 1 displayed a significantly decreased ear thickness compared to the RP treated mice on the first sensitization, but on the second challenge displayed similar levels of increased thickness (FIG. 23). Thus, the application of Peptide 1 with the DNFB displayed decreased thickness in the first sensitization, and also resulted in the same sensitization with a subsequent challenge of DNFB alone.

Brackets indicate groups compared by the students 2-tailed t-test. Statistically significant differences are indicated with asterisks (* $p<0.05$; ** $p<0.01$).

Example 10

Isomeric Forms of Peptide 1

Both the D- and L-isomeric forms of Peptide 1 were tested for their ability to decrease ear swelling in response to DNFB application. BALB/c mice were sensitized with 0.5% DNFB as described in Example 8 (FIG. 19) above and received subcutaneous injection of 40 μg/ear of either D- or L-isomeric form of Peptide 1 (closed circles) or RP (open circles) at 24 hr and 1 hr before elicitation with 0.2% DNFB. The data shown are the ear swelling responses (compared with the baseline thickness before DNFB application) over a 3 day period. As shown, both the L-isomer and the D-isomer decreased the ear swelling in response to the DNFB application as compared to the mice receiving the RP (FIG. 24).

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A composition comprising:
   a carrier material; and
   a peptide consisting essentially of an amino acid sequence selected from the group consisting of:
   i) Gly-Ala-His-Trp-Gln-Phe-Asn-Ala-Leu-Thr-Val-Arg (SEQ ID NO: 1) or a conservative amino acid substitution thereof at a residue position other than 4, 5, 6, 9, 10 or 11;
   ii) Gly-Ala-Ala-Trp-Gln-Phe-Asn-Ala-Leu-Thr-Val-Arg (SEQ ID NO: 7) or a conservative amino acid substitution thereof at a residue position other than 4, 5, 6, 9, 10 or 11;
   iii) Gly-Ala-His-Trp-Gln-Phe-Ala-Ala-Leu-Thr-Val-Arg (SEQ ID NO: 8) or a conservative amino acid substitution thereof at a residue position other than 4, 5, 6, 9, 10 or 11; and
   iv) Gly-Ala-His-Trp-Gln-Phe-Asn-Ala-Leu-Thr-Val-Ala (SEQ ID NO: 9) or a conservative amino acid substitution thereof at a residue position other than 4, 5, 6, 9, 10 or 11.

2. The composition of claim 1, wherein the carrier material is a pharmaceutically acceptable carrier.

3. The composition of claim 1, wherein the carrier material is a pharmaceutically acceptable injectable liquid.

4. The composition of claim 1, wherein the carrier material is a topical ointment.

5. The composition of claim 1, wherein the carrier material is a pharmaceutically acceptable carrier for oral dosage.

6. The composition of claim 1, wherein the peptide is present in the composition in an amount sufficient to inhibit binding of hyaluronic acid to a hyaluronic acid receptor.

7. The composition of claim 6, wherein the hyaluronic acid receptor is CD44.

8. The composition of claim 1, wherein an amino acid of the peptide is a D-amino acid.

9. The composition of claim 1, wherein the peptide is a synthetic peptide.

10. A composition comprising:
    a carrier material; and
    a peptide consisting essentially of the amino acid sequence Gly-Ala-His-Trp-Gln-Phe-Asn-Ala-Leu-Thr-Val-Arg (SEQ ID NO: 1) or a conservative amino acid substitution thereof at a residue position other than 4, 5, 6, 9, 10 or 11.

11. The composition of claim 10, wherein the carrier material is a pharmaceutically acceptable carrier.

12. The composition of claim 10, wherein the carrier material is a pharmaceutically acceptable injectable liquid.

13. The composition of claim 10, wherein the carrier material is a topical ointment.

14. The composition of claim 10, wherein the carrier material is a pharmaceutically acceptable carrier for oral dosage.

15. The composition of claim 10, wherein the peptide is present in the composition in an amount sufficient to inhibit binding of hyaluronic acid to a hyaluronic acid receptor.

16. The composition of claim 15, wherein the hyaluronic acid receptor is CD44.

17. The composition of claim 10, wherein an amino acid of the peptide is a D-amino acid.

18. The composition of claim 10, wherein the peptide is a synthetic peptide.

19. A method for inhibiting cell migration, said method comprising:
    contacting a cell with a composition comprising a carrier material and a peptide, the peptide consisting essentially of an amino acid sequence selected from the group consisting of:
    i) Gly-Ala-His-Trp-Gln-Phe-Asn-Ala-Leu-Thr-Val-Arg (SEQ ID NO: 1) or a conservative amino acid substitution thereof at a residue position other than 4, 5, 6, 9, 10 or 11;
    ii) Gly-Ala-Ala-Trp-Gln-Phe-Asn-Ala-Leu-Thr-Val-Arg (SEQ ID NO: 7) or a conservative amino acid substitution thereof at a residue position other than 4, 5, 6, 9, 10 or 11;
    iii) Gly-Ala-His-Trp-Gln-Phe-Ala-Ala-Leu-Thr-Val-Arg (SEQ ID NO: 8) or a conservative amino acid substitution thereof at a residue position other than 4, 5, 6, 9, 10 or 11; and
    iv) Gly-Ala-His-Trp-Gln-Phe-Asn-Ala-Leu-Thr-Val-Ala (SEQ ID NO: 9) or a conservative amino acid substitution thereof at a residue position other than 4, 5, 6, 9, 10 or 11;
    wherein the peptide binds selectively to a glycsoaminoglycan, that mediates cellular migration.
    wherein said contacting inhibits migration of the cell.

20. The method of claim 10, wherein the glycosoaminoglycan is selected from the group consisting of: hyaluronic acid, chondroitin sulfate A, chondroitin sulfate C, dermatan sulfate, heparin, keratin sulfate, keratosulfate, chitin, chitosan 1, and chitosan 2.

21. The method of claim 19, wherein the glycosoaminoglysan is hyaluronic acid (HA), and wherein the peptide inhibits an HA-CD44 mediated migration.

22. The method of claim 19, wherein the peptide inhibits migration of immune cells.

23. The method of claim 19, wherein the peptide is a peptide consisting essentially of the amino acid sequence Gly-Ala-His-Trp-Gln-Phe-Asn-Ala-Leu-Thr-Val-Arg (SEQ ID NO: 1) or a conservative amino acid substitution thereof at a residue position other than 4, 5, 6, 9, 10 or 11.

* * * * *